United States Patent [19]
Campbell et al.

[11] Patent Number: 4,837,334
[45] Date of Patent: Jun. 6, 1989

[54] PRECURSORS TO QUINOLONE INOTROPIC AGENTS

[75] Inventors: Simon F. Campbell, Deal; David A. Roberts, Sandwich, both of England

[73] Assignee: Pfizer Inc., New York, N.Y.

[21] Appl. No.: 125,037

[22] Filed: Nov. 23, 1987

Related U.S. Application Data

[60] Division of Ser. No. 844,448, Mar. 26, 1986, Pat. No. 4,728,653, which is a continuation-in-part of Ser. No. 737,363, May 23, 1985, abandoned.

[30] Foreign Application Priority Data

May 29, 1984 [GB] United Kingdom ................ 8413685
Oct. 26, 1984 [GB] United Kingdom ................ 8427167

[51] Int. Cl.4 .......................................... C07D 233/61
[52] U.S. Cl. ................... 548/346; 548/262; 548/264; 548/265; 548/266; 548/267; 548/269; 548/301; 548/319; 548/321; 548/322; 548/337; 548/340; 548/342; 548/343
[58] Field of Search .............. 548/346, 301, 319, 321, 548/322, 337, 340, 342, 343, 262, 264, 265, 266, 267, 269

[56] References Cited

U.S. PATENT DOCUMENTS 4,258,185  3/1981  Nakao et al. ...................... 544/114
4,277,479  7/1981  Nishi et al. ...................... 546/157 X

FOREIGN PATENT DOCUMENTS 0052016  5/1982  European Pat. Off. ........... 546/157
55-076872  6/1980  Japan ................................ 546/157
2086896  5/1982  United Kingdom ............... 546/157

Primary Examiner—Richard A. Schwartz
Attorney, Agent, or Firm—Peter C. Richardson; Lawrence C. Akers; J. Trevor Lumb

[57] ABSTRACT

A series of novel heterocyclic-substituted 2-(1H)-quinolone compounds have been prepared, including the 3,4-dihydro derivatives thereof, wherein the heterocyclic ring moiety is a pyrrolyl, imidazolyl, pyrazolyl, triazolyl or tetrazolyl group attached by a nitrogen atom of said group to the 5-, 6-, 7- or 8-positions of the quinolone ring. These particular compounds are useful in therapy as highly potent inotropic agents and therefore, are of value in the treatment of various cardiac conditions. Preferred member compounds include 6-(2,4-dimethylimidazol-1-yl)-8-methyl-2-(1H)-quinolone, 6-(2,4-dimethyl-5-nitroimidazol-1-yl)-8-methyl-2-(1H)-quinolone, 8-methyl-6-(tetrazol-1-yl)-2-(1H)-quinolone, 8-methyl-6-(1,2,4-triazol-4-yl)-2-(1H)-quinolone, and 6-(4-cyano-2-methylimidazol-1-yl)-8-methyl-2-(1H)-quinolone, respectively. Methods for preparing these compounds from known starting material are provided.

6 Claims, No Drawings

PRECURSORS TO QUINOLONE INOTROPIC AGENTS

This is a division of application Ser. No. 844,448, filed on Mar. 26, 1986, now U.S. Pat. No. 4,728,653, which in turn is a continuation-in-part of application Ser. No. 737,363, filed May 23, 1985, now abandoned.

BACKGROUND OF THE INVENTION

This invention relates to substituted guinolone cardiac stimulants which in general selectively increase the force of myocardial contraction without producing significant increases in the heart rate. The compounds are useful in the curative or prophylactic treatment of cardiac conditions, in particular heart failure.

SUMMARY OF THE INVENTION

Thus, according to the invention there are provided substituted 2-(1H)-quinolones of the formula:

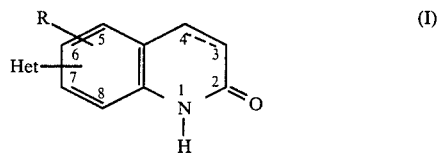

and their pharmaceutically acceptable salts, wherein "Het" is an optionally substituted 5-membered monocyclic aromatic hetrocyclic group containing at least one nitrogen atom in the aromatic ring and and attached by a nitrogen atom to the 5-, 6-, 7- or 8- position of said quinolone; R, which is attached to the 5-, 6-, 7- or 8- position, is hydrogen, $C_1$–$C_4$ alkyl, $C_1$–$C_4$ alkoxy, hydroxy, $CF_3$, halo, cyano or hydroxymethyl; and the dashed line between the 3- and 4-positions represents an optional bond.

Preferably, "Het" contains 1, 2, 3 or 4 nitrogen atoms (and no other heteroatoms) in the aromatic ring.

Examples of said group "Het" include pyrrolyl, imidazolyl, pyrazolyl, triazolyl and tetrazolyl, all optionally substituted by up to 3, preferably 1 or 2, substituents each independently selected from, e.g., $C_1$–$C_4$ alkyl, $C_1$–$C_4$ alkoxy, hydroxy, halo, $CF_3$, cyano, hydroxymethyl, ($C_1$–$C_4$ alkoxy)carbonyl, nitro, —$CONR^1R^2$ and —$NR^1R^2$ where $R^1$ and $R^2$ are each independently H or $C_1$–$C_4$ alkyl.

"Halo" means F, Cl, Br or I. $C_3$ and $C_4$ alkyl and alkoxy groups can be straight or branched chain. The preferred alkyl and alkoxy groups are methyl and methoxy.

Although the compounds of the formula (I) are written as 2-(1H)-quinolones, it should be realised that the following tautomerism will occur:

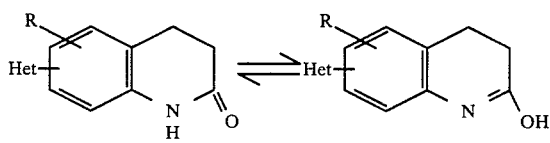

However, as the keto-form is considered the more stable tautomer, the end products herein will be named and illustrated as quinolones although those skilled in the art will realise that both tautomers may be present or that any particular compound so named may exist predominantly as the hydroxy tautomer and the following disclosure is to be interpreted to incorporate all tautomeric forms.

Preferably, there is a double bond in the 3,4-position.

R is preferably H, $C_1$–$C_4$ alkyl, $CF_3$ or halo attached to the 8-position of the quinolone ring. More preferably R is H, $CH_3$, $CF_3$ or Br. R is most preferably H or $CH_3$.

"Het" is preferably an imidazolyl, pyrazolyl, triazolyl or tetrazolyl group attached to the 6-position of the quinolone ring, said groups being optionally substituted by up to 3 substituents each selected from $C_1$–$C_4$ alkyl, $CF_3$, $NO_2$, $NH_2$, CN, and halo.

The preferred subsitutents on "Het" are $CH_3$, $CR_3$, $NO_2$, $NH_2$, CN, Br, or I. More preferably, "Het" is an imidazol-l-yl, 2-methylimidazol-1-yl, 4-methylimidazol-1-yl, 5-methylimidazol-1-yl, 1,2,4-triazol-1-yl, 2,4-dimethylimidazol-1-yl, pyrazol-1-yl, 4-trifluoromethylimidazol-1-yl, tetrazol-1-yl, 3,5dimethyl-1,2,4-triazol-1-yl, 3,5-dimethyl-1,2,4-triazol-4-yl, tetrazol-2-yl, 1,2,4-triazol-4-yl, 2,4-dimethyl-5-nitroimidazol-1-yl, 5-nitro-4-methylimidazol-1-yl, 5-amino-2,4-dimethylimidazol-1-yl, 5-bromo-2,4-dimethylimidazol-1-yl, 5-iodo-2,4-dimethylimidazol-1-yl, 5-cyano-2,4-dimethylimidazol-1-yl, 2-cyano-4-methylimidazol-1-yl, 4-cyano-2-methylimidazol-1-yl, 2-iodo-4-methylimidazol-1-yl or 4-iodo-2-methylimidazol-1-yl group.

Most preferably, "Het" is a 2,4-dimethyl-5-nitroimidazol-1-yl, 2,4-dimethylimidazol-1-yl, tetrazol-1-yl, 1,2,4-triazol-4-yl or 4-cyano-2-methylimidazol-1-yl group.

The most preferred individual compounds of the formula (I) have the formula:

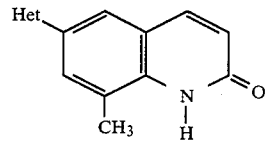

where Het is 2,4-dimethylimidazol-1-yl, 2,4-dimethyl-5-nitroimidazol1-yl, tetrazol-1-yl, 1,2,4-triazol-4-yl or 4-cyano-2-methylimidazol-yl.

The pharmaceutically acceptable salts of the compounds of the formula (I) are either acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, methanesulphonate and p-toluenesulphonate salts, or are metal salts, particularly the alkaline earth or alkalimetalsalts. The preferred metal salts are the sodium and potassium salts. All the salts are preparable by conventional techniques.

The cardiac stimulant activity of the compounds of the formula (I) is shown by their effectiveness in one or more of the following tests: (a) increasing the force in contraction in the "Starling" dog heart —lung preparation measured via a left ventricular catheter; (b) increasing myocardial contractility (left ventricular dp/dt max.) in the anaesthetised dog measured via a left ventricular catheter; (c) increasing myocardial contractility in the conscious dog with an implanted left ventricular transducer (dp/dt max.) or an exteriorised carotid artery loop (systolic time intervals).

In test (a), the positive inotropic effect of the test compound following bolus administration is measured in the "Starling" dog hear-lung preparation. The selectivity for increase in force versus frequency of contractioon of the test compound is obtained.

In test (b), the positive inotropic action of the test compound following intravenous administration is measured in the anaesthetised dog. The magnitude and duration of this action, and the selectivity for increase in force versus frequency of contraction of the test compound are obtained, as are the peripheral effects, e.g. the effect on blood pressure.

In test (c) the positive inotropic action of the test compound following intravenous or oral administration to a conscious dog with an implanted left ventricular transducer (dp/dt max.) or an exteriorised carotid artery loop (systolic time intervals) is measured. The magnitude of the inotropic action, the selectivity for increase in force versus frequency of contraction, and the duration of action of the inotropic effect of the test compound and all obtained.

The compounds of the formula (I) can be administered alone but will generally be administered in admixture with a pharmaceutical carrier selected with regard to the intended route of administration and standard pharmaceutical practice. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, it is expected that oral dosages of the compounds of the invention will be in the range from 10mg to 1g daily, taken in 2 to 4 divided doses per day, for an average adult patient (70kg). Dosages for intravenous administration would be expected to be within the range of 0.5 to 100mg per single dose as required, for example in the treatment of acute heart failure. Thus for a typical adult patient, individual tablets or capsules might contain 2.5 to 100mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of stimulating the heart of a human being, which comprises administering to said human a compound of formula (I) or pharmaceutically acceptable salt thereof, or a pharmaceutical composition as defined above, in an amount sufficient to stimulate the heart of said human.

The invention yet further provides a compound of the formula (I) or pharmaceutically acceptable salt thereof, for use in medicine, in particular for use in stimulating the heart of a human being suffering from congestive heart failure.

DETAILED DESCRIPTION OF THE INVENTION

The compounds of the formula (I) can be prepared by a number of routes, including the following:
Route A:
This method is illustrated as follows:

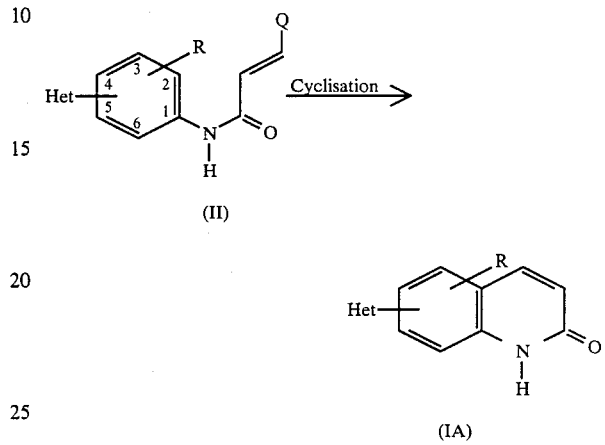

"Q" is a leaving group such as $C_1$–$C_4$ alkoxy.

The cyclisation is preferably carried out by treating the propenamide (II) with concentrated, desirably substantially anhydrous (98%), sulphuric acid at room temperature until the reaction is complete, typically in 6–48 hours. If necessary, heating at up to 100° C. can be carried out to speed up the reaction. The product can then be isolated and purified by conventional procedures. In the propenamide (II), Q is preferably ethoxy or methoxy.

The propenamide (II) can also be used in acid addition salt form (e.g. as a hydrochloride).

Typical reactions are illustrated as follows:

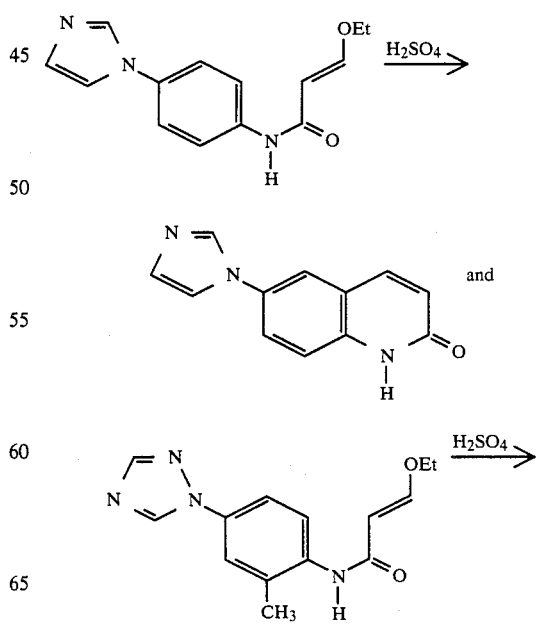

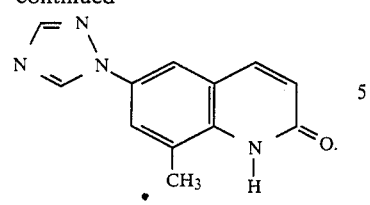

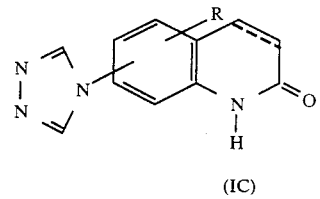

The starting materials of the formula (II) can be prepared by conventional procedures. A typical route to these materials, many of which are illustrated in detail in the following Preparations, is as follows:

The reaction is typically carried out by heating the reactants in a melt at 100°–250° C. until the reaction is complete.

A typical reaction is illustrated as follows:

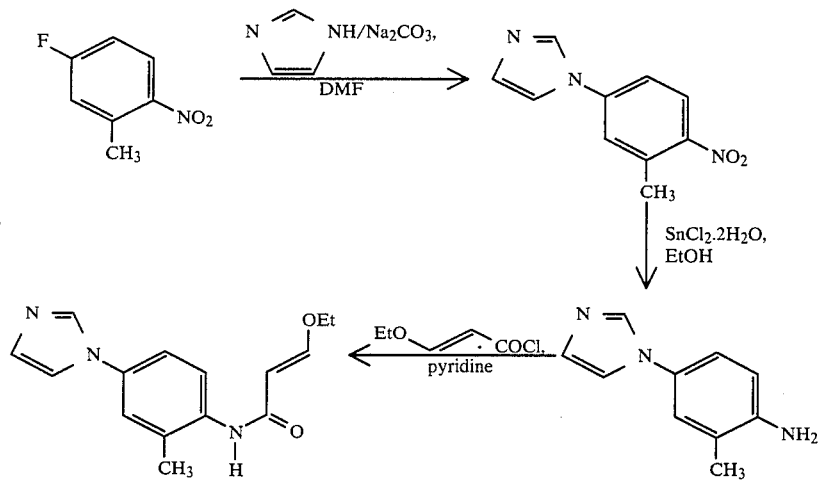

Route B:
This route can be illustrated in general terms as follows:

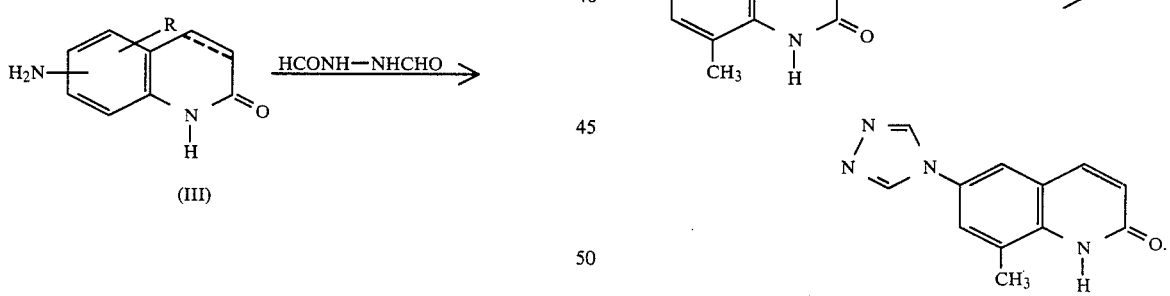

The starting materials (III) can be prepared by conventional procedures. A typical route to a starting materials is as follows:

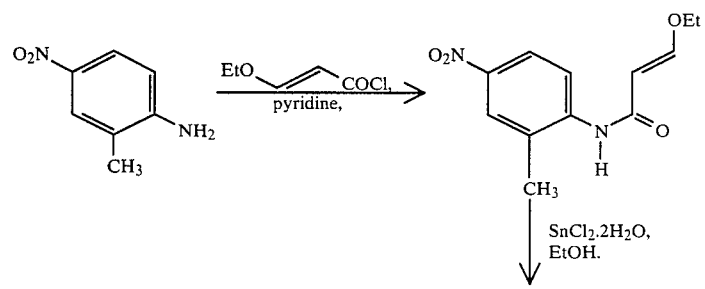

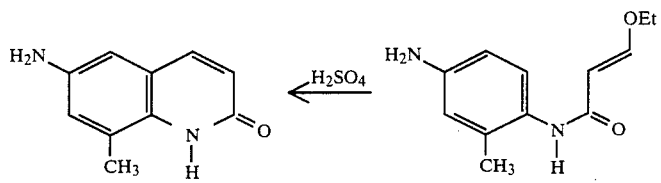

Route C:
This route can be illustrated in general terms as follows:

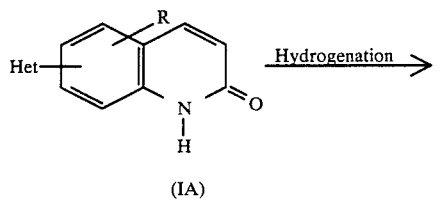

The reaction is typically carried out by hydrogenation of the starting material (IA) in a suitable organic solvent (e.g. ethanol) over a transition metal catalyst (e.g. 5-10% palladium on charcoal or platinum oxide) at 1-330 atmospheres pressure and at up to 100° C.

A typical reaction is illustrated as follows:

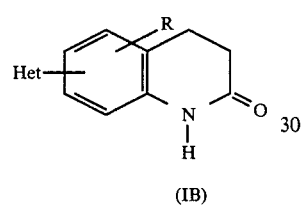

Route D:
This route can be illustrated in general terms as follows:

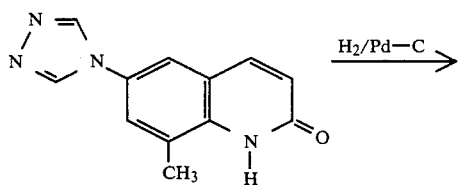

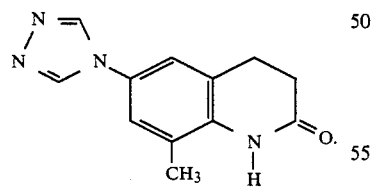

The demethylation is preferably carried out by heating the methoxyquinoline (IV) in aqueous mineral acid, preferably aqueous HCl or HBr, and typically in 5M aqueous HCl or 48% aqueous HBr at up to reflux temperature, generally for 0.5-4 hours. The product can then be isolated and purified by conventional means.

Typical reactions of this type are illustrated as follows:

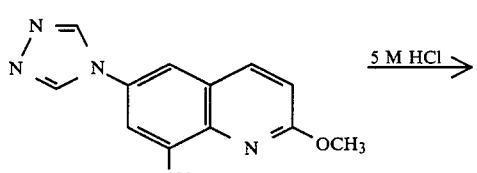

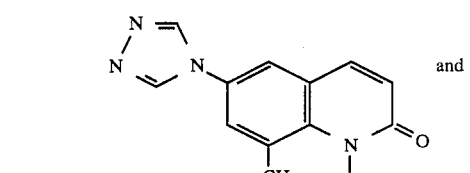

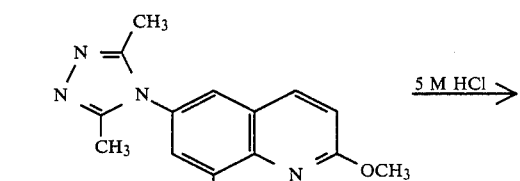

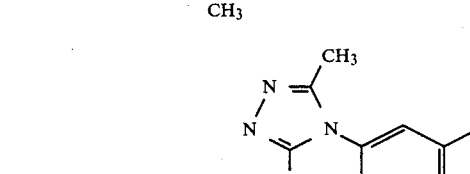

The starting materials of the formula (IV) can again be prepared by conventional procedures. Typical routes to these materials, many of which are illustrated in detail in the following Preparations, are as follows:

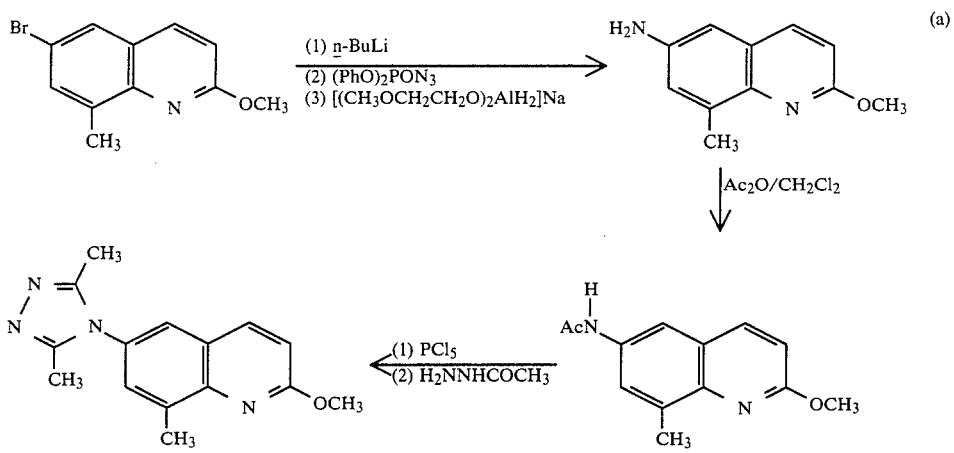

6-Bromo-2-methoxy-8-methylquinoline can be prepared by refluxing the corresponding 2-chloro compound with sodium methoxide in methanol for up to 24 hours.

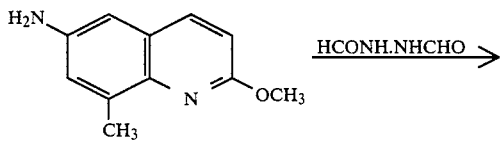

Route E:
This route can be illustrated in general terms as follows:

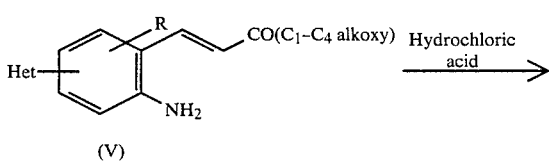

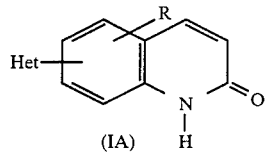

The reaction is typically carried out by heating the starting material (V), preferably as the methyl or ethyl ester, in 5M aqueous HCl at up to the reflux temperature, generally, for 0.5-4 hours. The product can then be isolated and purified by conventional means.

A typical reaction is illustrated as follows:

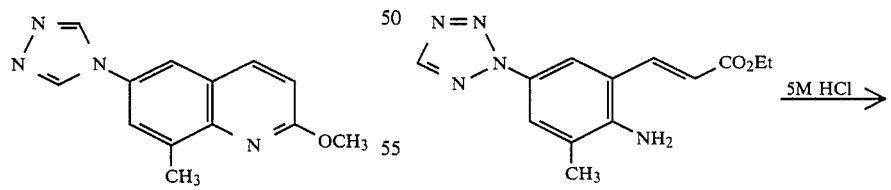

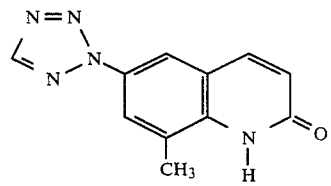

The starting materials (V) can be prepared by conventional procedures. A typical route to a starting material is as follows:

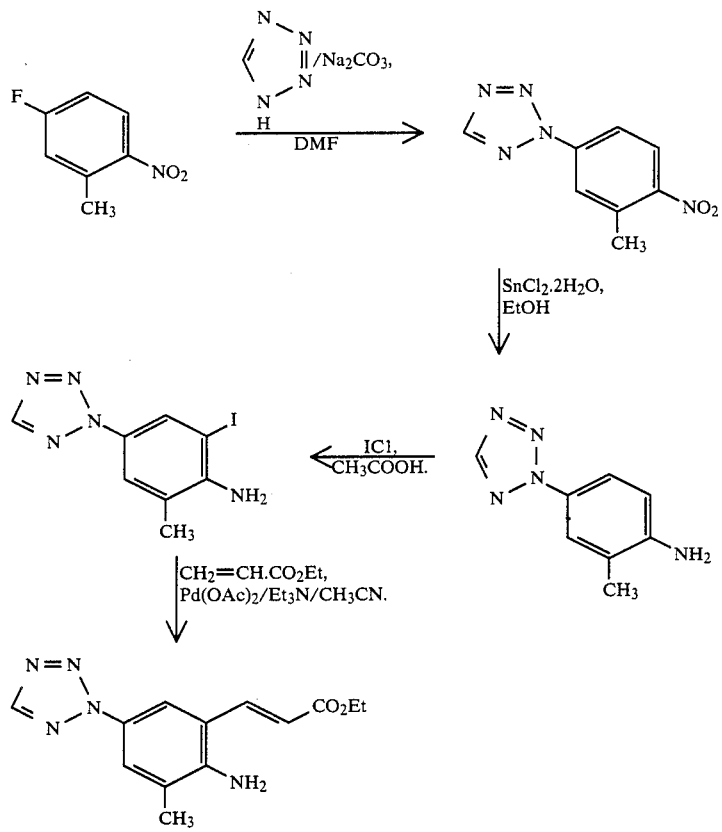

An alternative route to the starting materials (V) is outlined in Route J.

Route F:

This route can be illustrated in general terms as follows:

5–10% palladium on charcoal) at 1–4 atmospheres pressure and at up to 70° C. The hydrogenated intermediate (VI) is then heated in a suitable organic solvent (e.g. xylene) for, say, up to 48 hours and at a temperature of up to 200° C.

A typical reaction is illustrated as follows:

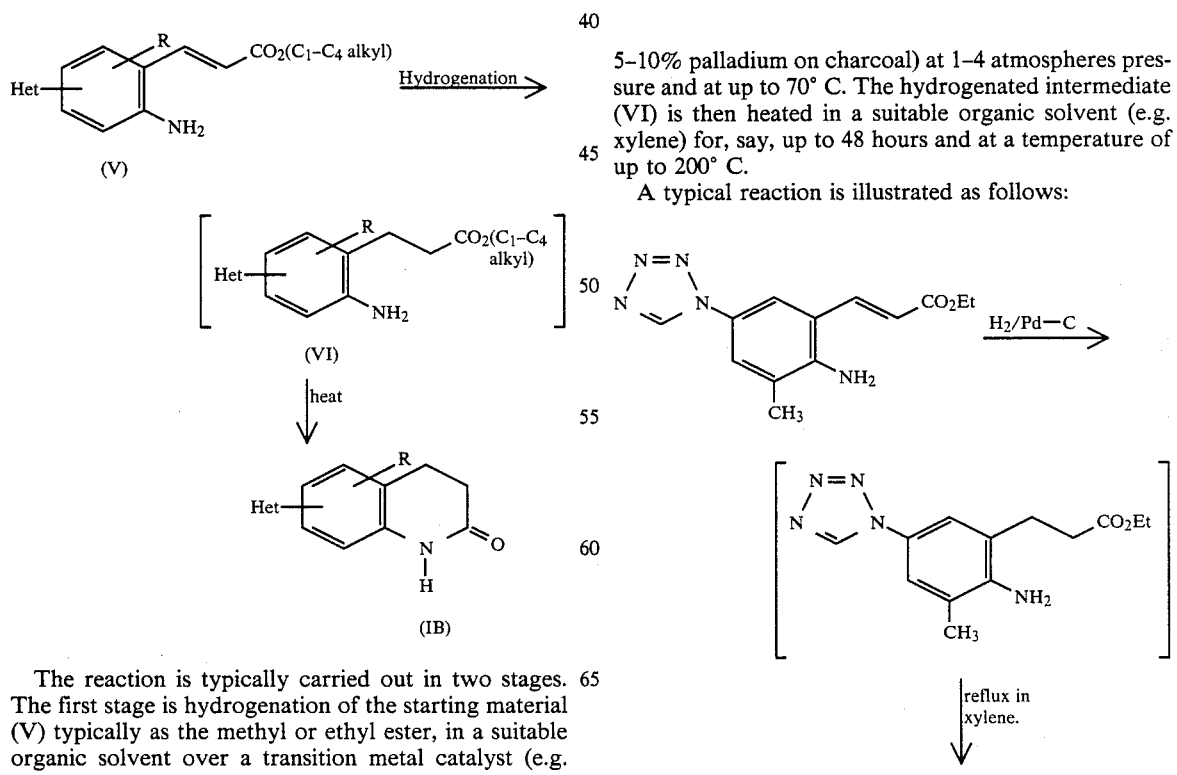

The reaction is typically carried out in two stages. The first stage is hydrogenation of the starting material (V) typically as the methyl or ethyl ester, in a suitable organic solvent over a transition metal catalyst (e.g.

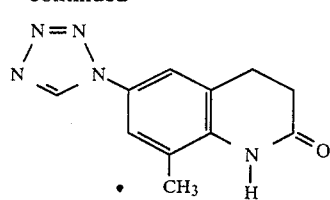

The starting materials (V) can be prepared by conventional procedures as outlined in Route E.

Route G:

This route to nitro-substituted heterocycles can be illustrated in general terms as follows:

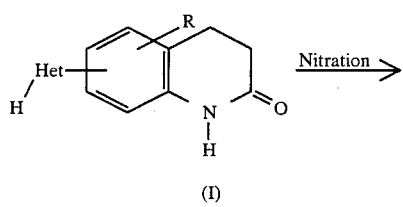

The reaction is typically carried out by nitration of the starting material (I) with a mixture of concentrated sulphuric and nitric acids, generally for, say, 0.5–2 hours at low temperature (−10° to +20° C.). The produt can then be isolated and purified by conventional means.

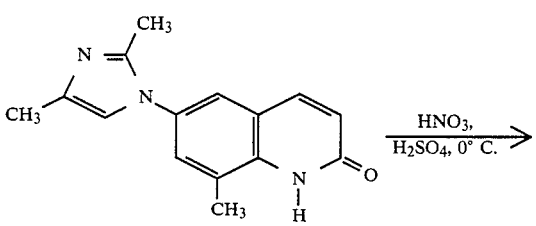

A typical reaction is illustrated as follows:

Route H:

This route to amino-substituted heterocycles can be illustrated in general terms as follows:

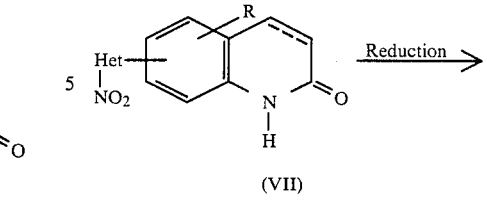

The reduction is typically carried out by the selective hydrogenation of the starting material (VII) in a suitable organic solvent, e.g. ethanol, over Raney nickel at 1–6 atmospheres pressure, and at up to about 70° C. The product can then be isolated and purified by conventional means.

A typical reaction is illustrated as follows:

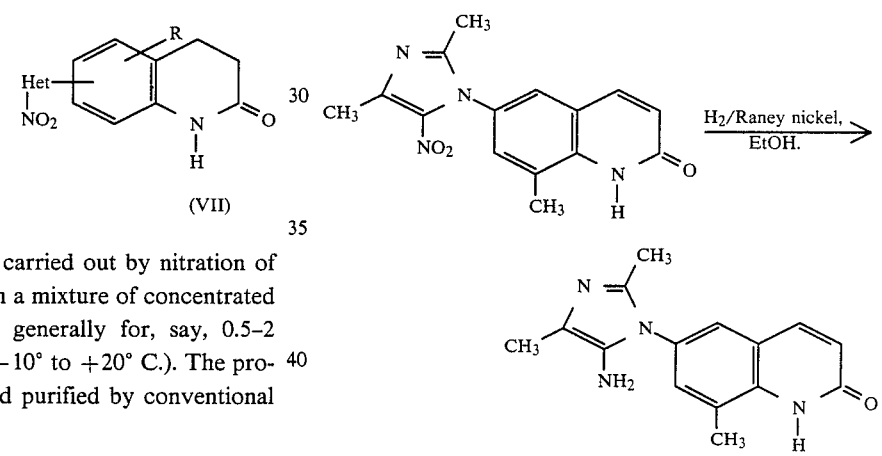

Route I:

This route to halo-substituted heterocycles can be illustrated in general terms as follows:

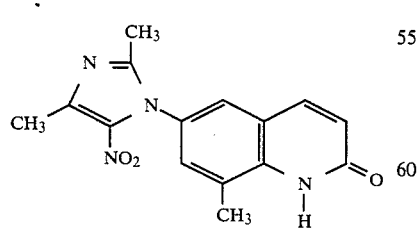

The reaction is typically carried out by halogenating the quinolone (IA) in a suitable organic solvent in a conventional manner. Typical halogenating agents are N-chlorosuccinimide, N-bromosuccinimide and iodine monochloride. The product can then be isolated and purified by conventional means.

A typical reaction is illustrated as follows:

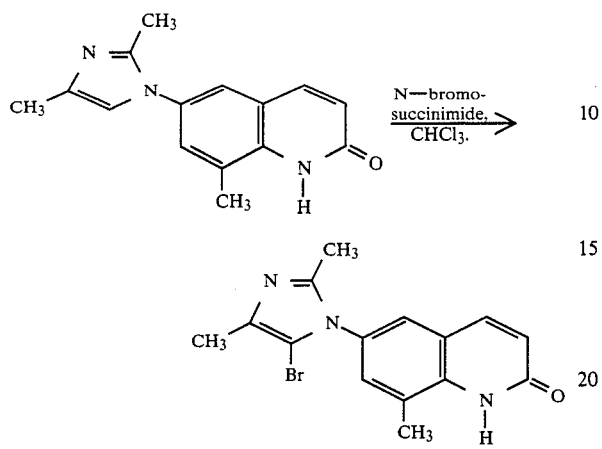

Route J:

This route can be illustrated in general terms as follows:

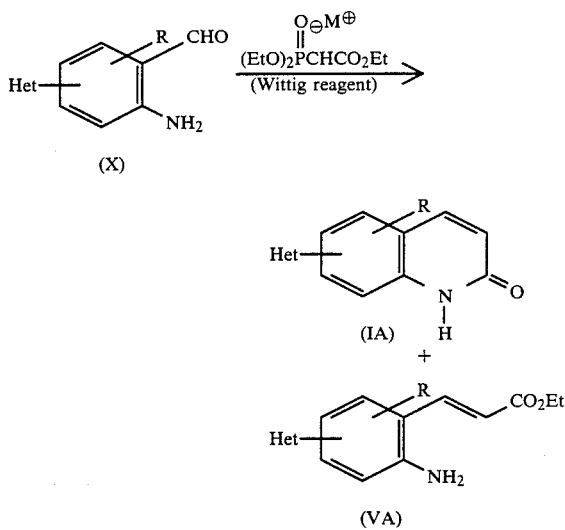

"M" is an alkali metal, preferably Na.

The reaction is typically carried out by heating the starting aldehyde (X) with the Wittig reagent in a suitable organic solvent, e.g. ethanol, at up to the reflux temperature, generally for 1-3 hours. The products can then be isolated and purified by conventional means.

A typical reaction is illustrated as follows:

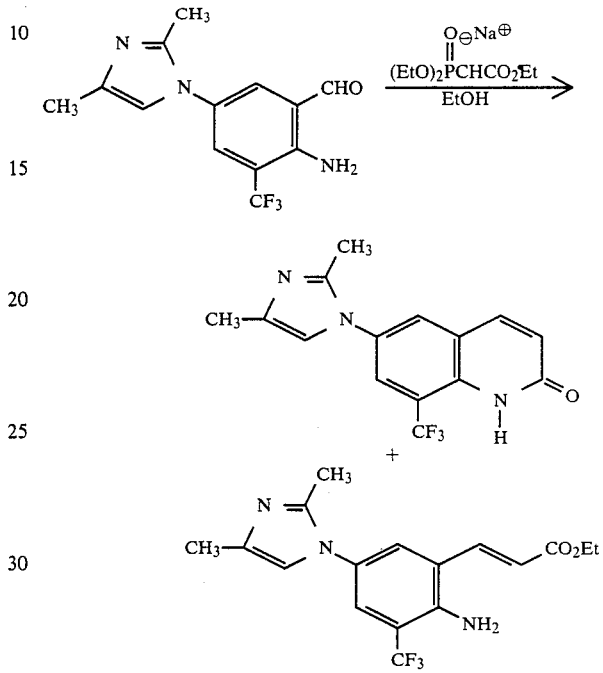

The starting materials (X) can be prepared by conventional procedures. A typical route to a starting material is as follows:

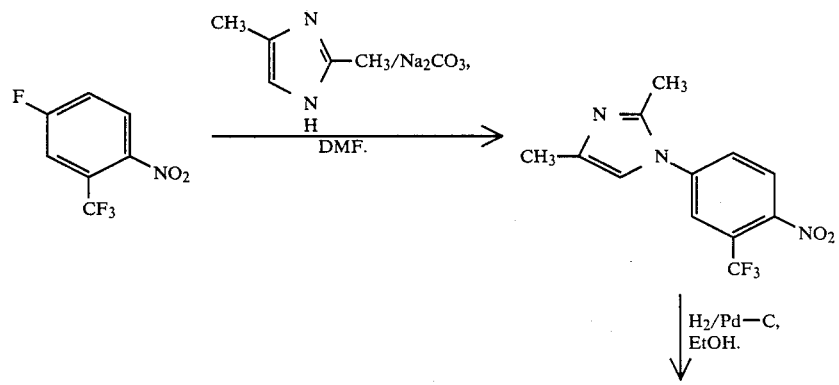

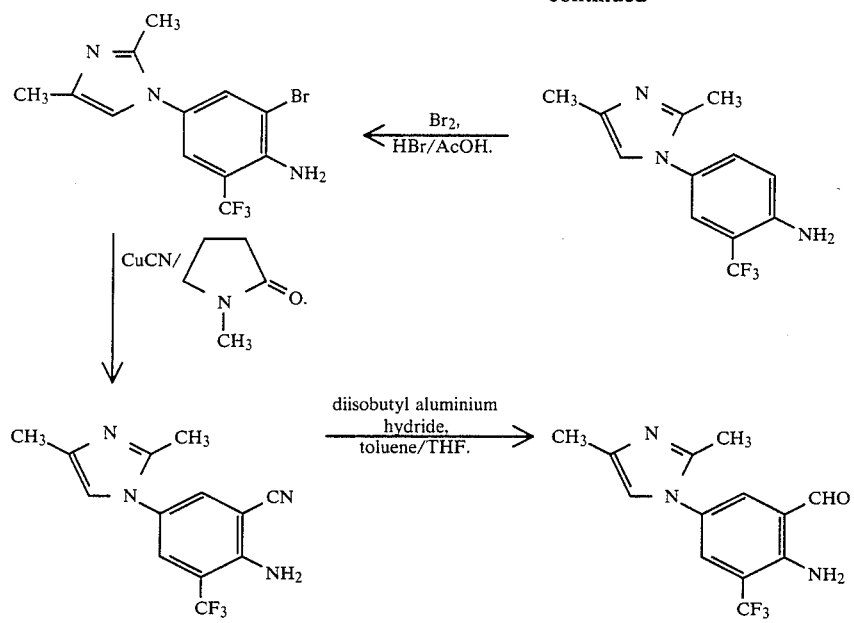

Route K:
This route to halo-substituted quinolones can be illustrated in general terms as follows:

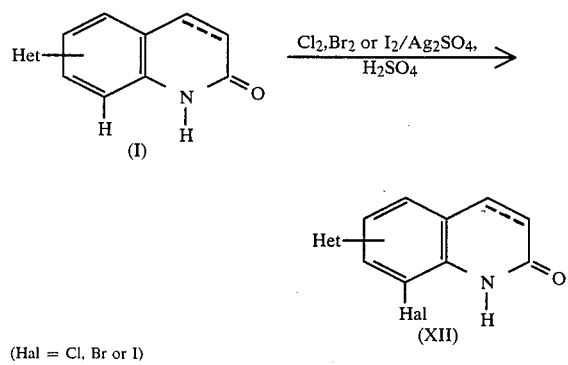

(Hal = Cl, Br or I)

The reaction is typically carried out by halogenation of the starting material (I) in 98% sulphuric acid and in the presence of silver sulphate. The product can be isolated and purified by conventional means.

A typical reaction is illustrated as follows:

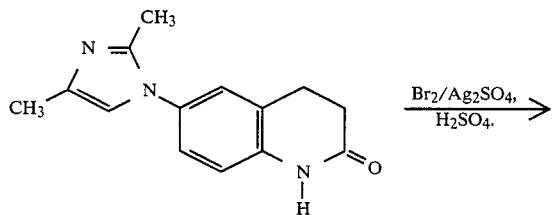

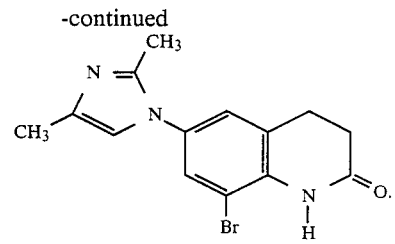

Route L:
Compounds having a cyano substituent on the group "Het" can be prepared either by (a) reaction of the corresponding amino-substituted compound with $H_2SO_4/NaNO_2/CuCN$ (Sandmeyer reaction) or (b) by reaction of the corresponding bromo- or iodosubstituted compound with a metal cyanide (e.g. CuCN or NaCN), and preferably in the presence of a catalyst such as $Pd(PPh_3)_4$ or $Pd(OAc)_2$.

Where the compounds of the invention contain one or more asymmetric centres, then the invention includes the separated enantiomers and diastereoisomers or mixtures thereof. The separated forms can be obtained by conventional means.

The following Examples illustrate the invention (all temperatures are in °C):

EXAMPLE 1

Preparation of 6-(1-imidazolyl)-8-methyl-2-(1H)-quinolone

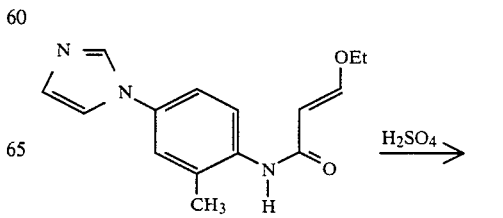

-continued

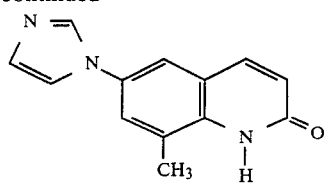

Trans-1-[4-{N-(3-ethoxypropenamido)}-3-methylphenyl]-imidazole (2.7 g) was added portionwise with stirring to 98% w/w sulphuric acid (20 cm³) at 0°. After 24 hours at room temperature (20° C.) the mixture was poured carefully onto ice (200 g) and the resulting solution was basified with saturated sodium carbonate solution to pH8. The resulting suspension was extracted with methanol:chloroform, 1:4 by volume, (7×200 cm³), and the combined and dried (MgSO₄) extracts were evaporated in vacuo to give a solid which was chromatographed on silica (Merck "MK 60.9385") eluting with methanol:chloroform, 1:19 by volume. Collection and evaporation of appropriate fractions afforded a white solid which was recrystallised from ethyl acetate/methanol to give 6-(1-imidazolyl)-8-methyl-2-[1H]-quinolone, m.p. 259°14 262° (1.71 g).

Analysis %: Found: C,69.2; H,4.9; N,18.3; Calculated for $C_{13}H_{11}N_3O$: C,69.3; H,4.9; N,18.6.

EXAMPLES 2–11

The following compounds were prepared similarly to Example 1, starting from the appropriately substituted trans-3-ethoxypropenamide (or hydrochloride thereof in Examples 4 and 5) and 98% (w/w) sulphuric acid:

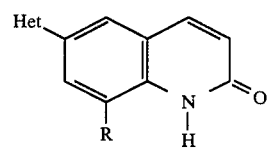

| Example No. | Het | R | Form isolated and m.p. (°C.) | Analysis % (Theoretical in brackets) | | |
|---|---|---|---|---|---|---|
| | | | | C | H | N |
| 2 | N=⟨  ⟩N– | —H | Free base, 250–260° (decomp.) | 68.0 (68.2 | 4.3 4.3 | 19.9 19.9) |
| 3 | CH₃ on imidazole | —H | Free base, 297° | 69.4 (69.3 | 5.0 4.9 | 18.9 18.6) |
| 4 | CH₃ on imidazole | —CH₃ | Free base, 295° | 70.3 (70.3 | 5.6 5.5 | 17.2 17.6) |
| 5 | CH₃-imidazole | —H | Free base, 253° | 69.4 (69.3 | 5.1 4.9 | 18.3 18.6) |
| 6 | CH₃-imidazole | —CH₃ | Free base, 292–5° | 69.8 (70.3 | 5.5 5.5 | 17.4 17.6) |
| 7 | CH₃-imidazole | —CH₃ | Free base, 255–259° (decomp.) | 69.9 (70.3 | 5.5 5.5 | 17.3 17.6) |
| 8 | triazole | —H | Free base, 266–269° (decomp.) | 61.8 (62.2 | 3.8 3.8 | 26.1 26.4) |
| 9 | triazole | —CH₃ | Free base, 318–321° | 64.1 (63.7 | 4.5 4.4 | 24.8 24.8) |

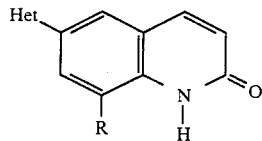

| Example No. | Het | R | Form isolated and m.p. (°C.) | Analysis % (Theoretical in brackets) | | |
|---|---|---|---|---|---|---|
| | | | | C | H | N |
| 10 | CH₃ imidazole with CH₃ | H | Free base 0.5H₂O, >300° | 67.9 (67.7 | 5.5 5.5 | 17.4 17.0) |
| 11 | pyrazole | —H | Free base, 244–245° | 67.9 (68.2 | 4.2 4.3 | 19.9 19.9) |

EXAMPLE 12

Preparation of 6-(2,4-dimethylimidazol-1-yl)-8-methyl-2-(1H)quinolone

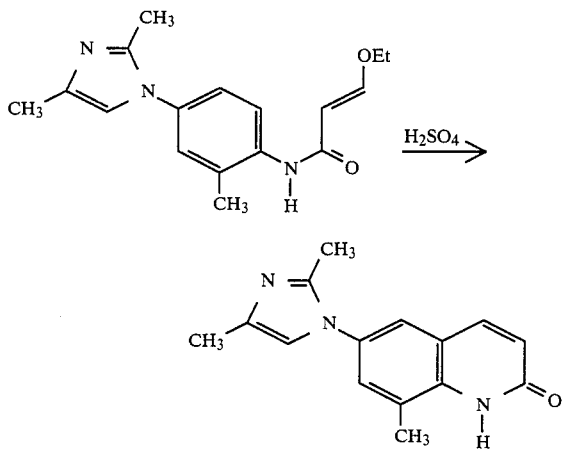

Trans-1-{4-[N-(3-ethoxypropenamido)]-3-methylphenyl}-2,4-dimethylimidazole (3.2 g) was added portionwise with stirring to 98% w/w sulphuric acid (15 cm³) at 0°. After 24 hours at room temperature (20°) the mixture was poured carefully onto ice (150 g) and the resulting solution was basified to pH8 with saturated aqueous sodium bicarbonate. The mixture was then extracted with methanol:chloroform, 1:9 by volume (6×100 cm³), and the combined and dried (MgSO₄) organic extracts were evaporated in vacuo to give a solid which was recrystallised from ethyl acetate/methanol to afford 6-(2,4-dimethylimidazol-1-yl)-8-methyl-2-(1H)-quinolone, m.p. 322.5°–325° (1.0 g).

Analysis %: Found: C,71.4; H,6.1; N,16.7; Calculated for C₁₅H₁₅N₃O: C,71.1; H,6.0; N,16.6.

EXAMPLES 13–17

The following compounds were prepared similarly to Example 12, starting from the appropriate trans-3-ethoxypropenamide and 98% w/w sulphuric acid:

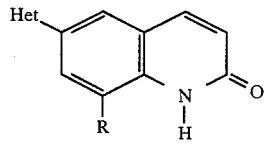

| Example No. | Het | R | Form isolated and m.p. (°C.) | Analysis % (Theoretical in Brackets) | | |
|---|---|---|---|---|---|---|
| | | | | C | H | N |
| 13 | CF₃-imidazole | —CH₃ | Free base, 0.25H₂O, 294° | 56.4 (56.5 | 3.5 3.5 | 14.2 14.1) |
| 14 | pyrazole | —CH₃ | Free base, 229–231° | 69.3 (69.3 | 5.1 4.9 | 18.4 18.7) |

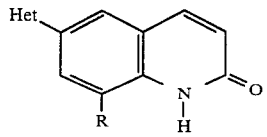

| Example No. | Het | R | Form isolated and m.p. (°C.) | Analysis % (Theoretical in Brackets) C | H | N |
|---|---|---|---|---|---|---|
| 15 | N=\<br>N\_/N— | —CH$_3$ | Free base 1.0H$_2$O, 365–369° | 59.6 (59.0 | 4.5 4.9 | 22.5 22.9) |
| 16 | N=N\<br>N\_/N— | —CH$_3$ | Free base 0.5H$_2$O, 267–268° | 56.2 (55.9 | 4.1 4.2 | 29.8 29.7) |
| 17 | CH$_3$\<br>N\_/N—<br>CH$_3$ | —CH$_3$ | Free base, 273–276° | 66.4 (66.1 | 5.6 5.6 | 22.1 22.0) |

EXAMPLE 18

Preparation of 3,4-dihydro-8-methyl-6-(1,2,4-triazol-1-yl)2-(1H)-quinolone

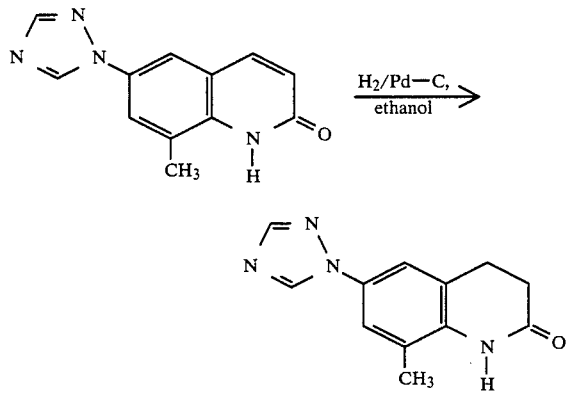

A suspension of 6-(1,2,4-triazol-1-yl)-8-methyl-2-(1H)-quinolone (see Example 9) (1.7g) in ethanol (450 cm$^3$) was hydrogenated at 60° and 60 p.s.i. (4.13×10$^5$ Pa) pressure over 10% palladised charcoal (0.35g) for 72 hours. The cooled mixture waas then filtered through "Solkafloc" (Trademark for a cellulose based filtering agent) and evaporated in vacuo to afford a solid. Chromatography on silica (Merck "MK 60.9385" [Trade Mark]) eluting with chloroform: methanol, 49:1, followed by combination and evaporation of the appropriate fractions in vacuo gave a solid which was recrystallised from ethyl acetate/methanol to give 3,4-dihydro-8-methyl-6-(1,2,4-triazol-1-yl)-2-(1H)-quinolone, m.p. 258°–259° (0.266 g).

Analysis %: Found: C,62.9; H,5.2; N,24.4; Calculated for C$_{12}$H$_{12}$N$_4$O: C,63.1; H,5.3; N,24.5.

EXAMPLES 19–23

The following compounds were prepared similarly to Example 18 by the hydrogenation of the appropriately substituted quinolone in ethanol over palladised charcoal:

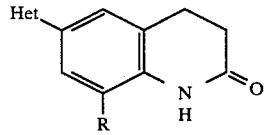

| Example No. | Het | R | Form isolated and m.p. (°C.) | Analysis % (Theoretical in Brackets) C | H | N |
|---|---|---|---|---|---|---|
| 19 | N=\<br>N\_/N— | —CH$_3$ | Free base 0.16H$_2$O, 334–336° | 62.5 (62.3 | 5.1 5.3 | 24.5 24.2) |

-continued

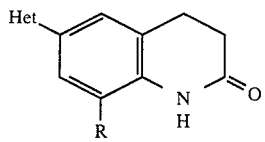

| Example No. | Het | R | Form isolated and m.p. (°C.) | Analysis % (Theoretical in Brackets) C | H | N |
|---|---|---|---|---|---|---|
| 20 | (CH3, CH3 triazole) | —CH3 | Free base, 260–262° | 70.4 (70.6 | 6.7 6.7 | 16.4 16.5) |
| 21 | (CH3 triazole) | —CH3 | Free base, 224–226° | 69.8 (69.7 | 6.3 6.3 | 17.2 17.4) |
| 22 | (CH3 triazole) | —CH3 | Free base, 233–235° | 69.3 (69.7 | 6.4 6.3 | 17.4 17.4) |
| 23 | (CH3, CH3 triazole) | —H | Free base 0.5H2O, 248–249° | 67.1 (67.2 | 6.2 6.5 | 16.7 16.8) |

EXAMPLE 24 (Alternative to Example 15)

Preparation of 8-methyl-6-(1,2,4-triazol-4-yl)-2-(1H)-quinolone ¼ hydrate

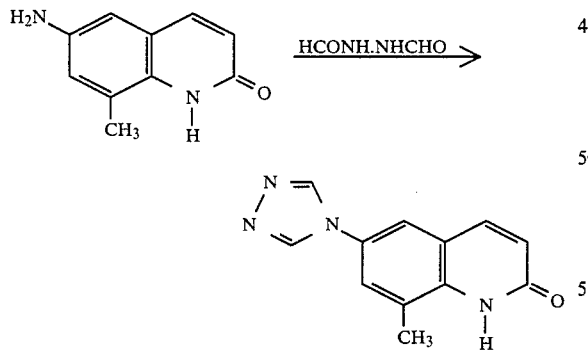

A mixture of 6-amino-8-methyl-2-(1H)-quinolone (0.485 g) and 1,2-diformylhydrazine (0.245 g) was stirred and heated in a melt at 200° for 1 hour. The residue was then triturated with hot isopropanol, cooled and filtered and the solid residue was recrystallised from chloroform-isopropanol to afford 6-(1,2,4-triazol-4-yl)-8-methyl-2-(1H)-quinolone 0.25 H2O, m.p. 369°–371° (0.112 g).

Analysis %: Found: C,62.7; H,4.3; N,23.8. Calculated for $C_{12}H_{10}N_4 \cdot 1/4 H_2O$: C,62.5; H,4.6; N,24.3.

EXAMPLE 25

Preparation of 6-[3,5-dimethyl-1,2,4-triazol-4-yl]-8-methyl-2(1H)-quinolone, 0.66 H2O

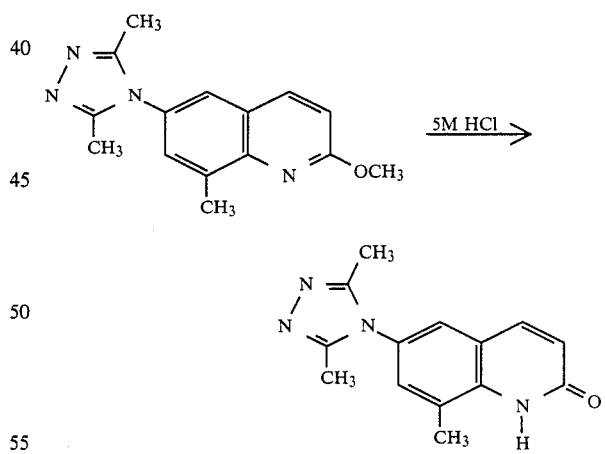

A stirred solution of 6-[3,5-dimethyl-1,2,4-triazol-4-yl]-2-methoxy-8-methylquinoline (0.24 g) in 5M hydrochloric acid (20 cm³) was heated under reflux for 1 hour. The cooled solution was then basified to pH8 with 10% aqueous sodium carbonate solution and extracted with chloroform (5×50 cm³). The combined and dried (MgSO4) organic phases were evaporated in vacuo and the residue was chromatographed on silica (Merck "MK 60.9385" [Trade Mark]) eluting with dichloromethane:methanol, 20:1, to afford 6-[3,5-dimethyl-1,2,4-triazol-4-yl]-8-methyl-2-(1H)-quinolone, 0.66 H2O, m.p. 208°–310° (0.17 g).

Analysis %: Found: C,63.4; H,5.4; N,21.2; Calculated for $C_{14}H_{14}N_4O.0.66\ H_2O$: C,63.2; H,5.8; N,21.1.

EXAMPLE 26

(Alternative to Examples 15 and 24)

Preparation of 8-methyl-6-(1,2,4-triazol-4-yl)-2-(1H)-quinolone hydrochloride ¼ hydrate The following compound, m.p. >350°, was prepared similarly to the previous Example, starting from 2-methoxy-8-methyl-6-(1,2,4-triazol-4-yl)-quinoline and 5M HCl, except that, after refluxing the methoxy starting material with 5M HCl and cooling, the hydrochloride ¼ hydrate crystallised out of solution and was filtered off and dried.

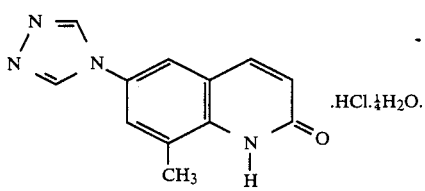

Analysis %: Found: C,54.1; H,4.4; N,21.2; Calculated for $C_{12}H_{10}N_4O.HCl.0.25\ H_2O$: C,54.0; H,4.3; N,21.0.

EXAMPLE 27

Preparation of 8-methyl-6-(tetrazol-2-yl)-2-(1H)-quinolone 1/4 hydrate

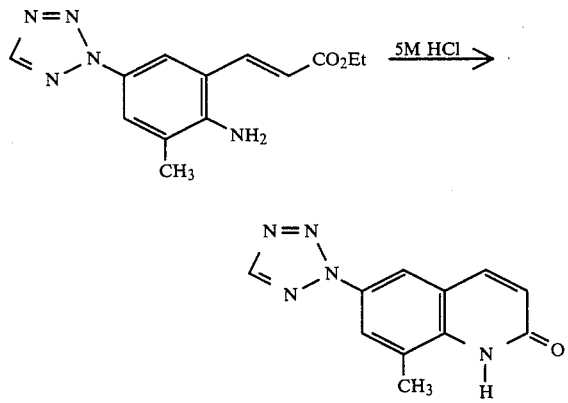

5M Hydrochloric acid (20 cm³) was added to trans-ethyl 3-(2-amino-3-methyl-5-[tetrazol-2-yl]phenyl)prop-2-enoate (0.45 g) and the mixture was heated on a steam bath for 1 hour. The mixture was then cooled, brought to pH 7 with aqueous sodium carbonate solution, and extracted with dichloromethane:methanol, 20:1 (3×50 cm³). The combined organic extracts were dried (MgSO₄), filtered and evaporated to dryness. The residue was chromatographed on silica (Merck "MK 60.9385" [Trade Mark]) eluting with ethyl/acetate:methanol, 10:1. Combination and evaporation of the appropriate fractions afforded 8-methyl-6-(tetrazol-2-yl)-2-(1H)-quinolone, 0.25 H₂O, m.p. 264°-266°, (0.08 g).

Analysis %: Found: C,57.0; H,4.1; N,30.2; Calculated for $C_{11}H_9N_5O.0.25\ H_2O$: C,57.3; H,4.1; N,30.2.

EXAMPLE 28

Preparation of 8-trifluoromethyl-6-(1,2,4-triazol-4-yl)-2-(1H)quinolone

The following compound, m.p. >320°, was prepared similarly to the previous Example, starting from trans-ethyl 3-(2-amino-3-trifluoromethyl-5-[1,2,4-triazol-4-yl]phen and 5M HCl.

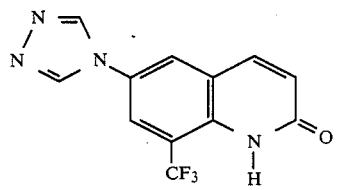

EXAMPLE 29

Preparation of 3,4-dihydro-8-methyl-6-(tetrazol-1-yl)-2-(1H)quinolone

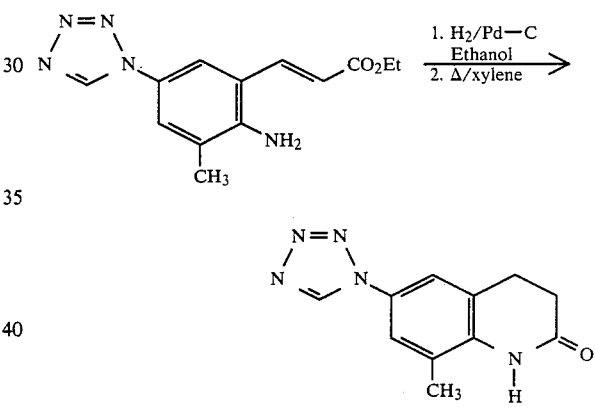

A suspension of trans-ethyl 3-(2-amino-3-methyl-5-[tetrazol1-yl]phenyl)prop-2-enoate (2.5 g) in ethanol (250 cm³) was hydrogenated at 60° and 15 p.s.i. (1.04×10⁵ Pa) pressure over 10% palladised charcoal (1 g) for 1½ hours. The cooled mixture was filtered through "Solkafloc" (Trade Mark) and evaporated in vacuo to afford a solid. A suspension of this solid in xylene (100 cm³) was heated under reflux for 7 hours. The mixture was then cooled and the product filtered off and washed with dichloromethane:methanol, 5:1, to afford 3,4-dihydro-8-methyl-6-(tetrazol-1-yl)-2-(1H)-quinolone, m.p. 271°-272°, (1.37 g).

Analysis %: Found: C,57.4; H,5.0; N,30.2; Calculated for $C_{11}H_{11}N_5O$: C,57.6; H,4.8; N,30.6.

EXAMPLES 30-32

The following compounds were prepared similarly to Example 29 using the appropriately substituted trans-ethyl 3-phenylprop-2-enoate derivative, hydrogen and palladised charcoal as the starting materials, followed by cyclisation of the resulting intermediate in refluxing xylene:

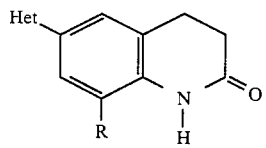

| Example No. | Het | R | Form isolated and m.p. (°C.) | Analysis % (Theoretical in Brackets) C | H | N |
|---|---|---|---|---|---|---|
| 30 | (tetrazole) N=N, N-N | $CH_3$ | Free base, 243–245° | 57.6 (57.6 | 4.9 4.8 | 30.0 30.6) |
| 31 | (2,4-dimethylimidazole) | $CF_3$ | Free base 0.25$H_2O$, 193–5° | 56.9 (56.6 | 4.5 4.7 | 13.2 13.2) |
| 32 | (1,2,4-triazole) | $CF_3$ | Free base, 264–7° | Structure confirmed by $^1H$ n.m.r. analysis. | | |

EXAMPLE 33

Preparation of 8-methyl-6-(2,4-dimethyl-5-nitroimidazol-1-yl)-2-(1H)-quinolone

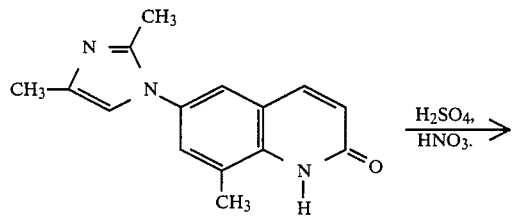

To a stirred solution of 8-methyl-6-(2,4-dimethylimidazol-1-yl)-2-(1H)-quinolone (0.5 g) in concentrated sulphuric acid (4 cm³) at 0° was added concentrated nitric acid (1 cm³). The mixture was stirred for 1 hour, poured carefully onto ice (100 g), and the solution basified to pH8 with solid sodium carbonate. The resulting suspension was extracted with dichloromethane (3 × 100 cm³) and the combined organic phases were dried (MgSO₄), filtered, and evaporated to yield a foam which was triturated with ethyl acetate/ether or afford 8-methyl-6-(2,4-dimethyl-5-nitro-imidazol-1-yl)-2-(1H)- m.p. 244°–247°, (0.52 g).

Analysis %: Found: C,60.0; H,4.8; N,19.3; Calculated for $C_{15}H_{14}N_4O_3$: C,60.4; H,4.7; N,18.8.

EXAMPLE 34

3,4-Dihydro-8-methyl-6-(2,4-dimethyl-5-nitroimidazol-1-yl)-2-(1H)-quinolone monohydrate, m.p. 198°–201°, was prepared similarly to Example 33 by the nitration of the corresponding 3,4-dihydroquinolone starting material.

Analysis %: Found: C,56.5; H,5.2; N,18.1; Calculated for $C_{15}H_{16}N_4O_3.H_2O$: C,56.8; H,5.4; N,17.7.

EXAMPLE 35

Preparation of 8-methyl-6-(5-amino-2,4-dimethylimidazol-1-yl)-2-(1H)-quinolone dihydrochloride ¼ hydrate

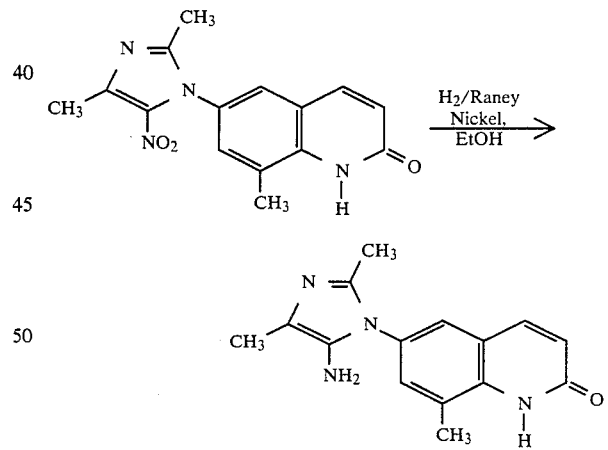

A suspension of 8-methyl-6-(2,4-dimethyl-5-nitroimidazol-1-yl)-2-(1H)-quinolone (2.26 g) in ethanol (50 cm³) was hydrogenated at 60° C. and 60 p.s.i. (4.13 × 10⁵Pa) pressure over Raney nickel (0.2 g) for 3 hours. The cooled mixture was then filtered through "Solkafloc" (Trade Mark) and evaporated in vacuo to afford a dark oil which solidified on trituration with isopropanol/ethyl acetate to afford a solid (2 g.). A small amount of solid was dissolved in ethanol, triturated with ethereal hydrogen chloride to give, after filtration, 8-methyl-6-(5-amino-2,4-dimethylimidazol-1-yl)-2-(1H)-quinolone dihydrochloride 1/4 hydrate, m.p. 223°.

Analysis %: Found: C,52.3; H,5.2; N,16.1; Calculated for $C_{15}H_{16}N_4O \cdot 2HCl \cdot 0.25 H_2O$: C,52.7; H,5.4; N,16.2.

EXAMPLE 36

Preparation of 8-methyl-6-(5-bromo-2,4-dimethylimidazol-1-yl)-2-(1H)-quinolone

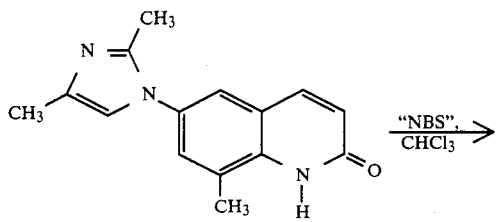

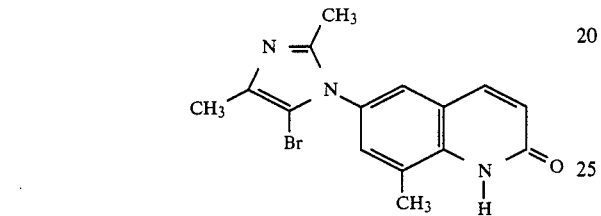

To a stirred suspension of 8-methyl-6-(2,4-dimethylimidazol1-yl)-2-(1H)-quinolone (0.5 g) in chloroform (10 cm³) was added N-bromosuccinimide (NS) (0.374 g) at room temperature. After 5 minutes the reaction mixture was evaporated to dryness and the residue chromatographed on silica (Merck "MK 60.9385" [Trade Mark]) eluting with ethyl acetate:methanol, 10:1. Combination and evaporation of the appropriate fractions afforded a solid which on recrystallisation from ethyl acetate/methanol gave 8-methyl-6-(5-bromo-2,4-dimethylimidazol-1-yl)-2-(1m.p. 273°, (0.277 g).

Analysis %: Found: C,54.2; H,4.2; N,12.7; Calculated for $C_{15}H_{14}N_3OBr$: C,54.2; H,4.3; N,12.7.

EXAMPLE 37

Prepartion of 8-trifluoromethyl-6-(2,4-dimethylimidazol-1-yl)-2-(1H)-quinolone

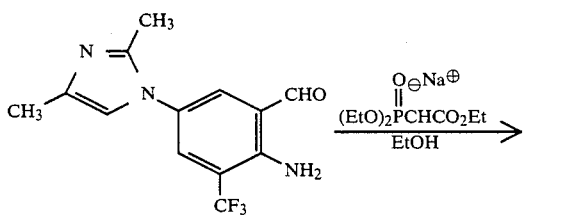

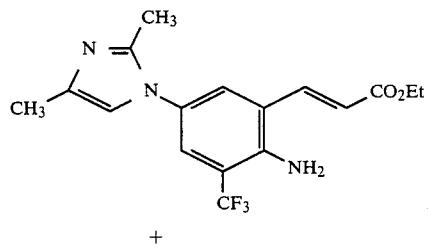

+

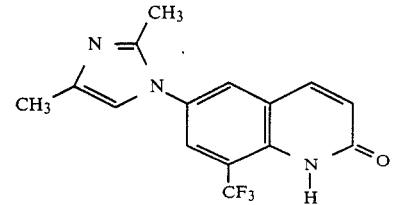

Triethyl phosphonoacetate (0.376 g) was added to a stirred suspension of sodium hydride (0.076 g) in ethanol (4 cm³). After 30 minutes a solution of 1-(4-amino-3-formyl-5-trifluoromethylphenyl)-2,4-dimethylimidazole (0.375 g) in ethanol (6 cm³) was added and the mixture was heated at reflux for 1½ hours. The mixture was cooled, partitioned between water (100 cm³) and chloroform (100 cm³) and the aqueous layer re-extracted with more chloroform (100 cm³). The combined organic extracts were dried (MgSO₄), filtered and evaporated to afford a yellow solid. This solid was chromatographed on silica (Merck "MK 60.9385" [Trade Mark]) eluting with ethyl acetate:methanol, 100:8. First to be eluted was trans-ethyl 3-(2-amino-3-trifluoromethyl-5-[2,4-dimethylimidazol-1-yl]phenyl)prop-2-en m.p. 181°–2°, (0.268 g), $R_F$=0.36 in ethyl acetate:methanol, 20:1. This intermediate was used in the method of Example 31.

Analysis %: Found: C,56.4; H,5.1; N,11.7; Calculated for $C_{17}H_{18}F_3N_3O_2$: C,57.8; H,5.1; N,11.9.

Further elution gave 8-trifluoromethyl-6-(2,4-dimethylimidazol-1-yl)-2-(1H)-quinolone as a yellow oil, crystallised from ether, m.p. 230°–3°, (0.05 g), $R_F$=0.1 in ethyl acetate:methanol, 20:1.

Analysis %: Found: C,58.2; H,4.2; N,13.3; Calculated for $C_{15}H_{12}F_3N_3O$: C,58.6; H,3.9; N,13.7.

EXAMPLE 38

Preparation of 8-bromo-6-(2,4-dimethylimidazol-1-yl)-3,4-dihydro2-(1H)-quinolone

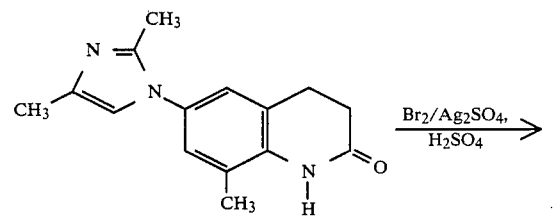

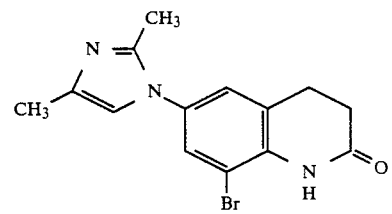

To a stirred solution of 6-(2,4-dimethylimidazol-1-yl)-3,4-dihydro-2-(1H)-quinolone (0.2 g) in concentrated sulphuric acid (5 cm³) was added bromine (0.045 cm³) and silver sulphate (0.186 g). The mixture was stirred at room temperature for 16 hours, poured onto ice (20 g.) and the mixture brought to pH 10 with aqueous 5M sodium hydroxide solution and extracted with dichloromethane (100 cm³). The organic extract was dried (MgSO₄), filtered and evaporated in vacuo to yield a white solid. This solid was recrystallised from ethyl acetate to give 8-bromo-6-(2,4-dimethylimidazol-1-yl)-3,4-dihydro-2-(1H)-qu (0.15 g), m.p. 242°.

Analysis %: Found: C,52.3; H,4.4; N,12.8; Calculated for C₁₄H₁₄BrN₃0: C,52.5; H,4.4; N,13.1.

EXAMPLE 39

8-Methyl-6-(5-nitro-4-methylimidazol-1-yl)-2-(1H)-quinolone. ¼H₂0, m.p. 306°-309°, was prepared similarly to Example 33 by the nitration of 8-methyl-6-(4-methylimidazol-1-yl)-2-(1H)-quinolone (see Example 6).

Analysis %: Found: C,58.3; H,4.4; N,19.8; Calculated for C₁₄H₁₂N₄O₃.1/4 H₂0: C,58.2; H,4.4; N,19.4.

EXAMPLE 40

Preparation of 8-methyl-6-(5-iodo-2,4-dimethylimidazol-1-yl)2-(1H)-quinolone, 0.5 H₂0

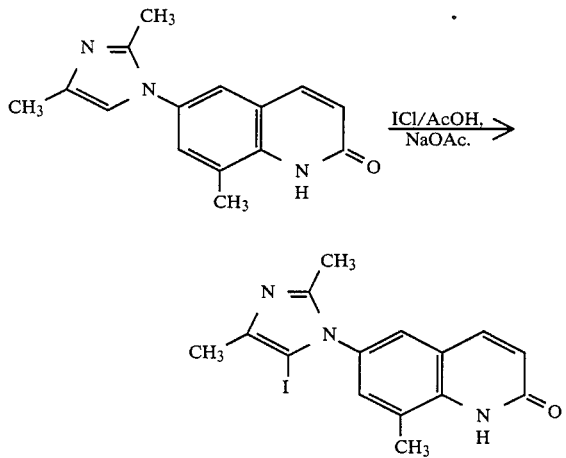

Iodine monochloride (0.406 g) was added at room temperature to a stirred solution of 8-methyl-6-(2,4-dimethylimidazol-1-yl)-2-(1H)-quinolone (0.506 g) and sodium acetate (0.328 g) in acetic acid (10 cm³). After 16 hours, volatile material was removed in vacuo and the residue partitioned between aqueous 2M sodium carbonate solution (50 cm³) and dichloromethane (50 cm³). The aqueous phase was further extracted with dichloromethane (2×50 cm³) and the combined and dried (MgSO₄) organic extracts were filtered and evaporated in vacuo. The residue was chromatographed on silica (Merck "MK 60.9385" [Trade Mark]) eluting with ethyl acetate. Combination and evaporation of the appropriate fractions afforded a solid which was recrystallised from ethyl acetatemethanol to give the title compound, m.p. 242°-245° (0.38 g).

Analysis %: Found: C,46.4; H,3.7; N,11.0; Calculated for C₁₅H₁₄IN₃0, 1/2 H₂0: C,46.4; H,3.9; N,10.8.

EXAMPLE 41

Preparation of 8-methyl-6-(2,4-dimethylimidazol-1-yl)-2-(1H)quinolone, methanesulphonate salt

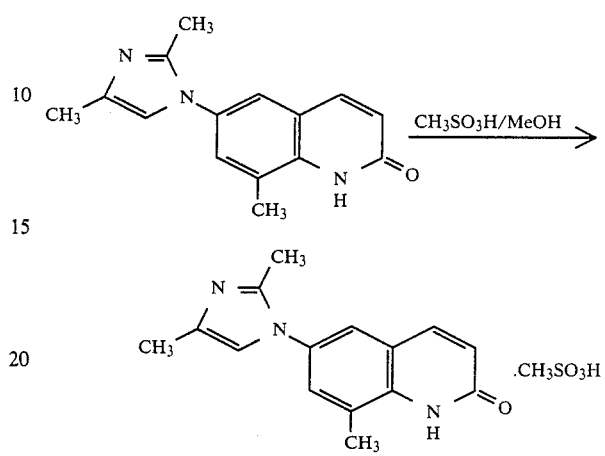

A stirred solution of 8-methyl-6-(2,4-dimethylimidazol-1-yl)-2-(1H)-quinolone (365.7 g) in methanol (914 cm³) at 60° was treated with methanesulphonic acid (141.9 g) over 5 minutes. Ethyl acetate (3.4 l) was added and the solution was allowed to cool to room temperature for 1 hour followed by cooling in an ice bath for 2 hours. The solid was filtered off, washed with ethyl acetate (450 cm³) and dried in vacuo at 50° to afford the title compound, m.p. 282°-284°.

Analysis %: Found: C,55.0; H,5.6; N,12.2; Calculated for C₁₆H₁₉N₃O₄S: C,55.0; H,5.5; N,12.0.

EXAMPLE 42

Preparation of 8-methyl-6-(5-cyano-2,4-dimethylimidazol-1-yl)-2(1H)-quinolone, ¼H₂0

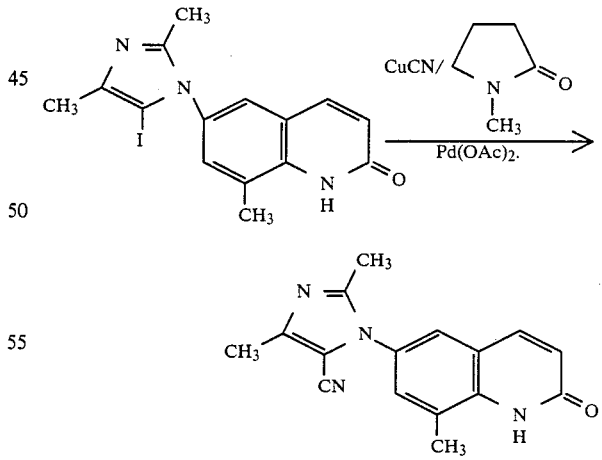

A mixture of 8-methyl-6-(2,4-dimethyl-5-iodoimidazol-1-yl)-2-(1H)-quinolone (0.1 g), cuprous cyanide (0.047 g) and palladium acetate (0.01 g), in N-methyl-2-pyrrolidone (1 cm³) was heated and stirred at 175° for 3 hours. The cooled mixture was poured into aqueous ammonia solution (10 cm³; S.G. 0.880) and dichloromethane (50 cm³) and the aqueous phase was further extracted with dichloromethane (2×50 cm³).

The combined and dried (MgSO₄) organic extracts were filtered and evaporated in vacuo and the residue was chromatographed on silica (Merck "MK 60.9385" [Trade Mark]) eluting with dichloromethane:methanol, 19:1. Combination and evaporation of appropriate fractions afforded an oil which crystallised on trituration with ether to give the title compound, m.p. 334°–337° (0.03 g).

Analysis %: Found: C,68.0; H,5.1; N,20.1; Calculated for $C_{16}H_{14}N_4O.1/4\ H_2O$: C,68.0; H,5.3; N,19.8.

The following Preparations illustrate the synthesis of the novel starting materials used in the preceding Examples. All temperatures are in °C:

PREPARATION 1

Trans-1-[4-{N-(3-ethoxypropenamido)}-3-methylphenyl]imidazole

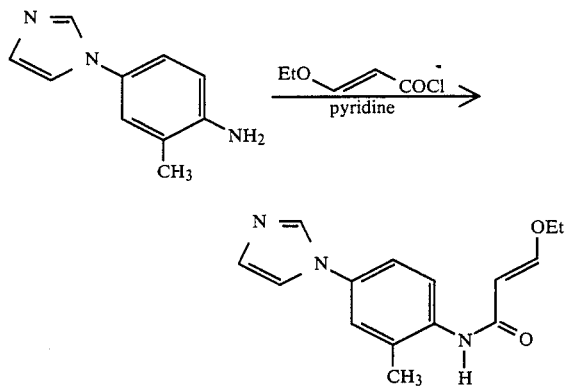

Trans-3-ethoxypropenoyl chloride (3.685 g) was added dropwise at 0° to a stirred solution of 1-(4-amino-3-methylphenyl)imidazole (4.325 g) in anhydrous pyridine (30 cm³). After stirring for 4 hours at room temperature, pyridine was removed in vacuo and the residue was partitioned between chloroform (150 cm³) and saturated sodium carbonate solution (20 cm³). The aqueous phase was further extracted with chloroform (2×50 cm³) and the combined and dried (MgSO₄) extracts were evaporated to afford an oil which was chromatographed on silica (Merck "MK 60.9385") eluting with methanol:chloroform, 3:97 by volume. Collection and evaporation of appropriate fractions afforded an oil whch crystallised on trituration with ethyl acetate/ether to yield the title compound, m.p. 141°–144°, (2.75 g).

Analysis %: Found: C,69.0; h,6.4; N,24.0; Calculated for $C_{15}H_{17}N_3O_2$: C,69.3; H,6.4; N,24.3.

PREPARATIONS 2–11

The following compounds were prepared similarly to the previous Preparation using the appropriately substituted anilines as starting materials:

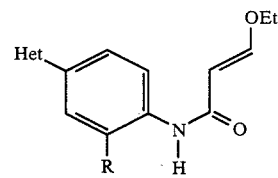

The anilines used in Preparations 2, 3, 8 and 11 are known compounds. The preparation of the remaining anilines is described in later Preparations in this text.

| Preparation No. | Het | R | Form isolated and m.p. (°C.) | Analysis % (Theoretical in brackets) | | |
|---|---|---|---|---|---|---|
| | | | | C | H | N |
| 2 | imidazol-1-yl | —H | Free base, 185–188° | 64.8 (65.4 | 5.8 5.9 | 16.3 16.3) |
| 3 | 2-methylimidazol-1-yl | —H | Free base, 174° | 66.6 (66.4 | 6.3 6.3 | 15.6 15.5) |
| 4* | 2-methylimidazol-1-yl | —CH₃ | Monohydrochloride, 260° | 59.3 (59.7 | 6.3 6.2 | 13.1 13.0) |
| 5* | 5-methylimidazol-1-yl | —H | Monohydrochloride, 244° | 58.3 (58.6 | 5.8 5.6 | 13.5 13.7) |
| 6 | 5-methylimidazol-1-yl | —CH₃ | Free base, 181–3° | 67.3 (67.3 | 6.8 6.7 | 14.6 14.7) |
| 7 | 4-methylimidazol-1-yl | —CH₃ | Free base, 131–3° | 67.2 (67.3 | 6.7 6.7 | 14.8 14.7) |

-continued

| Preparation No. | Het | R | Form isolated and m.p. (°C.) | Analysis % (Theoretical in brackets) C | H | N |
|---|---|---|---|---|---|---|
| 8 | imidazole* | —H | Free base, 177–180° | 60.5 (60.5 | 5.5 5.5 | 21.9 21.7) |
| 9 | imidazole | —CH₃ | Free base, 163–165° | 61.8 (61.8 | 5.8 5.8 | 20.6 20.6) |
| 10 | 2,4-dimethylimidazole | —H | Monohydrochloride, 267° | 59.9 (59.7 | 6.3 6.3 | 13.1 13.1) |
| 11 | pyrazole | —H | Free base, 183–186° | 65.4 (65.4 | 5.9 5.8 | 16.4 16.3) |

*These intermediates were purified directly by evaporation of the pyridine solvent in vacuo followed by chromatography of the crude hydrochloride salts on silica.

These intermediates were purified directly by evaporation of the pyridine solvent in vacuo followed by chromatography of the cruce hydrochloride salts on silica.

PREPARATION 12

1-(4-Amino-3-methylphenyl)imidazole

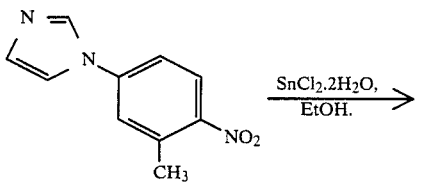

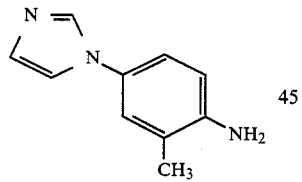

Stannous chloride dihydrate (55.0 g) was added portionwise to a stirred suspension of 1-(3-methyl-d4-nitrophenyl)imidazole (10.0 g) in absolute ethanol (100 cm³). After heating under reflux for 4 hours, the cooled mixture was basified to pH8 with aqueous 2.5 M sodium hydroxide solution and filtered. The filtrate was evaporated in vacuo, partitioned between chloroform (100 cm³) and water (50 cm³), and the aqueous phase was further extracted with chloroform (3×50 cm³). The combined and dried (MgSO₄) extracts were concentrated in vacuo to give a solid which was recrystallised from ethyl acetate to afford 1-(4-amino-3-methylphenyl)imidazole, m.p. 131°–134°, (4.7 g).

Analysis %: Found: C,69.0; H,6.4; N,24.0; Calculated for $C_{10}H_{11}N_3$: C,69.3; H,6.4; N,24.3.

PREPARATIONS 13–18

The following compounds were prepared similarly to the previous Preparation using the appropriately substituted nitrobenzene derivative and stannous chloride dihydrate as the starting materials:

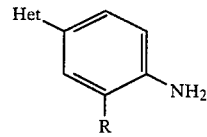

The nitrobenzene starting material used in Preparation 14 is a known compound. The preparation of the remaining nitrobenzenes is described in later Preparations in this text.

| Preparation No. | Het | R | Form isolated and m.p. (°C.) | Analysis % (Theoretical in brackets) C | H | N |
|---|---|---|---|---|---|---|
| 13 | 2-methylimidazole | —CH₃ | 0.25 H₂O, 166° | 69.4 (69.1 | 7.1 7.1 | 22.3 22.0) |
| 14 | 2-methylimidazole | —H | Free base, 132° | 69.0 (69.1 | 6.4 6.4 | 24.1 24.2) |

-continued

| Preparation No. | Het | R | Form isolated and m.p. (°C.) | Analysis % (Theoretical in brackets) C | H | N |
|---|---|---|---|---|---|---|
| 15 | ![structure](N=/CH3-C=N) | —CH₃ | Free base, 109–111.5° | 70.5 (70.6 | 7.0 7.0 | 22.3 22.4) |
| 16* | ![structure] | —CH₃ | Free base, 162–6° | 70.4 (70.6 | 7.0 7.0 | 22.3 22.4) |
| 17 | ![structure] | —CH₃ | Free base, 122–125° | 61.9 (62.1 | 5.9 5.8 | 32.1 32.2) |
| 18 | ![structure] | —H | Free base, 120° | 70.5 (70.6 | 7.1 7.0 | 21.8 22.4) |

*This compound was obtained as a mixture with the intermediate of Preparation 15. The mixture was separated by chromatography on silica (Merck "MK 60.9385") eluting with chloroform:methanol, 49:1 by volume. Combination and evaporation of the appropriate fractions in vacuo, followed by recrystallisation, gave the pure product.

This compound was obtained as a mixture with the intermediate of Preparation 15. The mixture was separated by chromaography on silica (Merck "MK 60.9385") eluting with chloroform:methanol, 49:1 by volume. Combination and evaporation of the appropriate fractions in vacuo, followed by recrystallisation, gave the pure product.

PREPARATION 19

6-Amino-8-methyl-2-(1H)-quinolone, m.p. 290° (decomp.), was prepared similarly to the method of Example 1 by the ring closure of trans-N-(4-amino-2-methylphenyl)-3-ethoxypropenamide using concentrated sulphuric acid.

Analysis %: Found: C,56.7; H,5.3; N,13.3; Calculated for $C_{10}H_{10}N_2O$: C,57.0; H,5.2; N,13.3.

Said propenamide, m.p. 140°–2°, was in turn prepared by the stannous chloride dihydrate reduction of the corresponding 4-nitro derivative according to the method of Preparation 12.

Analysis %: Found: C64.8; H,7.4; N,12.2; Calculated for $C_{12}H_{16}N_2O_2 \cdot 1/8\ H_2O$: C,64.8; H,7.3; N,12.6.

The 4-nitro derivative, i.e., trans-N-(4-nitro-2-methylphenyl)-3-ethoxypropenamide, m.p. 171°–3°, was prepared by the reaction of 2-methyl-4-nitroaniline with trans-3-ethoxypropenoyl chloride according to the procedure of Preparation 1.

Analysis %: Found: C,57.9; H,5.8; N,11.3; Calculated for $C_{12}H_{13}N_2O_4$: C,56.6; H,5.6; N,11.2.

PREPARATION 20

1-(3-Methyl-4-nitrophenyl)imidazole

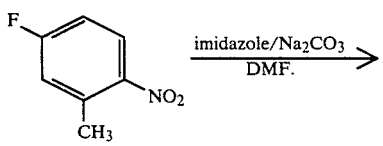

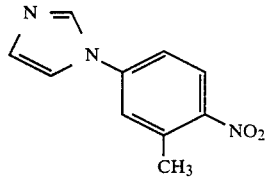

A mixture of 4-fluoro-3-methylnitrobenzene (15.5 g), imidazole (6.8 g), and sodium carbonate (11.1 g) was heated at 100° for 24 hours in dimethylformamide (DMF). The mixture was then concentrated in vacuo, the residue was acidified to pH1 with 4M hydrochloric acid, and the resulting solution was extracted with chloroform (2×25 cm³). The aqueous phase was basified to pH10 with 2.5 M sodium hydroxide solution and the mixture was extracted with chloroform (3×100 cm³). The dried (MgSO₄) organic extracts were evaporated to give a solid which was recrystallised from ethyl acetate to afford 1-(3-methyl-4-nitrophenyl)imidazole, m.p. 112°–115°, (10.0 g).

Analysis %: Found: C,58.9; H,4.4; N,20.7; Calculated for $C_{10}H_9N_3O_2$: C,59.1; H,4.5; N,20.7.

PREPARATIONS 21 14 25

The following compounds were prepared similarly to the previous Preparation using the appropriately substituted fluoronitrobenzene, the appropriate heterocycle and sodium carbonate as the starting materials:

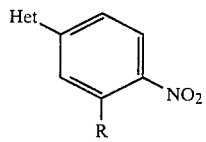

| Preparation No. | Het | R | Form isolated and m.p. (°C.) | Analysis % (Theoretical in brackets) C | H | N |
|---|---|---|---|---|---|---|
| 21 | 2-methyl-1-imidazolyl (CH₃ on C2) | —CH₃ | Free base, 135° | 60.9 (60.8 | 5.1 5.1 | 19.1 19.3) |
| 22 | 4-methyl-1-imidazolyl | —CH₃ | Free base 144–147° | 61.0 (60.8 | 5.1 5.1 | 19.6 19.3) |
| 23 | 5-methyl-1-imidazolyl | —CH₃ | Crude free base, solid. | Not characterized | | |
| 24 | 1,2,4-triazol-1-yl | —CH₃ | Free base, 116–117° | 52.9 (52.9 | 3.9 3.9 | 27.6 27.5) |
| 25 | 2,4-dimethyl-1-imidazolyl | —H | Free base 189° | 61.0 (60.8 | 5.2 5.1 | 19.1 19.4) |

PREPARATION 26

Trans-1-[4-{N-(3-ethoxypropenamido)}-3-methylphenyl]-2,4-dimethylimidazole

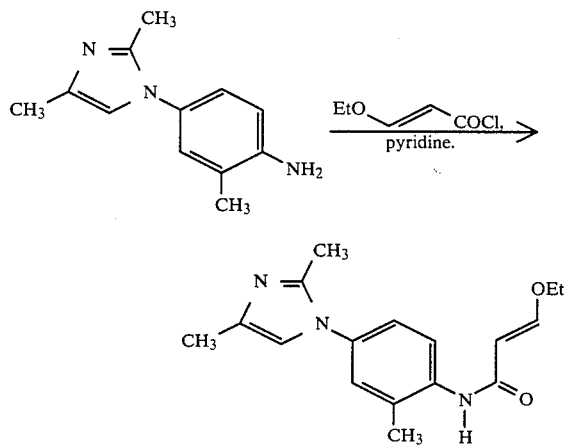

Trans-3-ethoxypropenoyl chloride (4.56 g) was added dropwise at 0° to a stirred solution of 1-(4-amino-3-methylphenyl)-2,4-dimethylimidazole (6.5 g) in anhydrous pyridine (40 cm³). After stirring for 2 hours at room temperature, pyridine was removed in vacuo and the residue was partitioned between chloroform (150 cm³) and saturated aqueous sodium carbonate solution (30 cm³). The aqueous phase was further extracted with chloroform (2×100 cm³) and the combined and dried (MgSO₄) organic extracts were evaporated to afford an oil which was chromatographed on silica (Merck "MK 60.9385" [Trade Mark]) eluting with methanol: chloroform, 1:19 by volume. Combination and evaporation of appropriate fractions afforded an oil which crystallised on trituration with ether to afford the title compound (6.3 g). Recrystallisation of a small portion from ethyl acetate gave microcrystals, m.p. 142.5°–144.5°.

Analysis %: Found: C,68.6; H,7.1; N,13.9; Calculated for $C_{17}H_{21}N_3O_2$: C,68.2; H,7.1; N,14.0.

PREPARATIONS 27-31

The following compounds were prepared similarly to the previous Preparation using the appropriately substituted aniline (as the hydrochloride in Preparations 27 and 28) and trans-3-ethoxypropenoyl chloride as the starting materials:

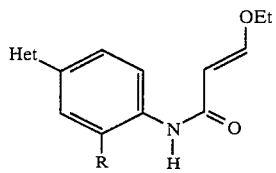

| Preparation No. | Het | R | Form isolated and m.p. (°C.) | Analysis % (Theoretical in Brackets) | | |
|---|---|---|---|---|---|---|
| | | | | C | H | N |
| 27 | (imidazole with CF₃, N=, N−) | —CH₃ | Free base, 194° | 56.4 (56.6 | 4.9 4.8 | 12.5 12.4) |
| 28 | (pyrazole, N, N−) | —CH₃ | Free base, 159–160° | 66.3 (66.4 | 6.3 6.3 | 15.3 15.5) |
| 29 | (triazole, N=, N, N−) | —CH₃ | Free base, 207–209° | 61.8 (61.8 | 6.1 5.9 | 20.9 20.6) |
| 30 | (tetrazole, N=N, N, N−) | —CH₃ | Free base, 179–181° | 57.2 (57.1 | 5.7 5.5 | 25.4 25.6) |
| 31 | (imidazole CH₃, N, N−, CH₃) | —CH₃ | Free base, 0.5H₂O 152–153.5° | 62.6 (62.5 | 6.6 6.2 | 18.2 18.2) |

PREPARATION 32

1-(4-Amino-3-methylphenyl)2,4-dimethylimidazole

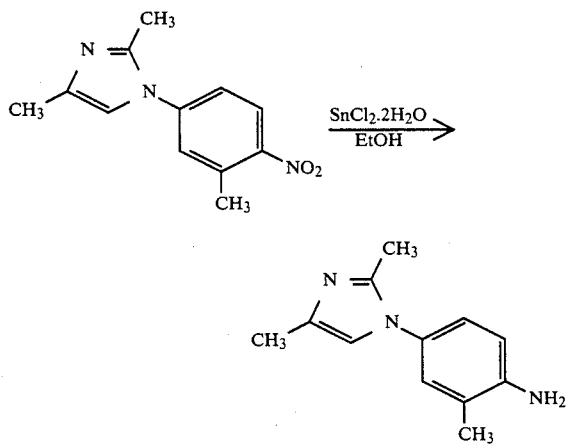

Stannous chloride dihydrate (40.7 g) was added portionwise to a stirred suspension of 1-(3-methyl-4-nitrophenyl)-2,4-dimethylimidazole (8.3 g) in absolute ethanol (100 cm³). After heating under reflux for 4 hours, the cooled mixture was basified to pH8 with aqueous 2.5 M sodium hydroxide and filtered. The filtrate was evaporated in vacuo, partitioned between chloroform (200 cm³) and water (50 cm³), and the aqueous phase was further extracted with chloroform (2×100 cm³). The combined and dried (MgSO₄) organic extracts were concentrated in vacuo to give a solid (6.8 g) which was recrystallised from ethyl acetate to afford 1-(4-amino-3-methylphenyl)-2,4-dimethylimidazole, m.p. 92°–96°.

PREPARATIONS 33–36

The following compounds were prepared similarly to the previous Preparation using the appropriately substituted nitrobenzene derivative and stannous chloride dihydrate as the starting materials.

In Preparation 33, the free base was converted to the hydrochloride salt by reaction with hydrogen chloride in ether. The hydrochloride was used in the next stage (Preparation 28).

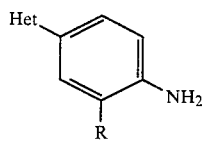

| Preparation No. | Het | R | Form isolated and m.p. (°C.) | Analysis % (Theoretical in Brackets) | | |
|---|---|---|---|---|---|---|
| | | | | C | H | N |
| 33 | (pyrazolyl) | —CH₃ | Monohydrochloride 0.25 H₂O, 263–266° | 56.4 (56.1 | 5.7 5.8 | 19.7 19.6) |
| 34 | (1,2,3-triazolyl) | —CH₃ | Free base, 100–103° | 54.9 (54.9 | 5.3 5.1 | 40.0 39.8) |
| 35 | (dimethylimidazolyl) | —CH₃ | Free base, 140–142° | 65.0 (65.3 | 6.7 7.0 | 27.5 27.7) |
| 36 | (tetrazolyl) | —CH₃ | Free base, 110–112° | 54.6 (54.9 | 5.1 5.1 | 39.8 40.0) |

PREPARATION 37

4-(4-Amino-3-methylphenyl)-1,2,4-triazole

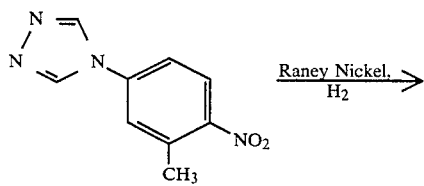

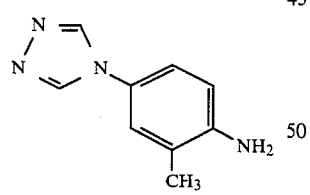

A solution of 4-(3-methyl-4-nitrophenyl)-1,2,4-triazole (1.0 g) in acetic acid (25 cm³) was hydrogenated at 25° and 60 p.s.i. (4.13×10¹⁵Pa) pressure over Raney nickel (0.2 g) for 2 hours. The mixture was then filtered through "Solkafloc" (Trade Mark for a cellulose based filtering agent), the solvent was evaporated in vacuo and the residue was partitioned between chloroform (100 cm³) and aqueous sodium carbonate solution (20 cm³). The aqueous phase was further extracted with chloroform (3×50 cm³) and the combined and dried (MgSO₄) organic extracts were concentrated to afford an oil which was chromatographed on silica (Merck "MK 60.9385" [Trade Mark]) eluting with methanol-:ethyl acetate, 1:9. Combination and evaporation of the appropriate fractions afforded a solid which was recrystallised from ethyl acetate/hexane to give 4-(4-amino-3-methylphenyl)-1,2,4-triazole, m.p. 152°–154° (0.67 g).

Analysis %: Found: C,62.0; H,5.6; N,31.8; Calculated for C₉H₁₀N₄: C,62.1; H,5.7; N,32.2.

PREPARATION 38

The following compound, m.p. 230°, was prepared similarly to the previous Preparation using 1-(3-methyl-4-nitrophenyl)-4-trifluoromethylimidazole and Raney nickel/H₂ as the starting materials but using ethanol instead of acetic acid as the solvent. The product was converted to the hydrochloride salt by reaction with hydrogen chloride in ether.

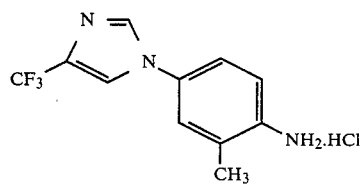

This hydrochloride salt was used in the next stage (Preparation 27).

Analysis %: Found: C,47.5; H,4.1; N,15.2; Calculated for C₁₁H₁₀F₃N₃.HCl: C,47.6; H,4.0; N,15.1.

PREPARATION 39

1-(3-Methyl-4-nitrophenyl)-2,4-dimethylimidazole

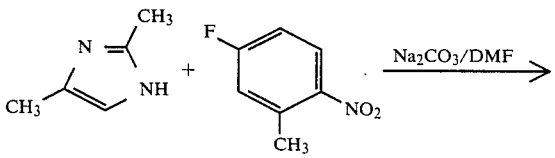

PREPARATIONS 40-44

The following compounds were prepared similarly to the previous Preparation using the appropriately substituted fluoronitrobenzene, the appropriate heterocycle and sodium carbonate as the starting materials:

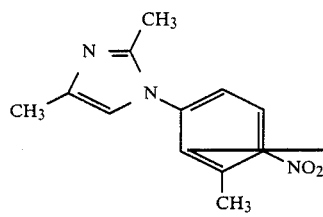

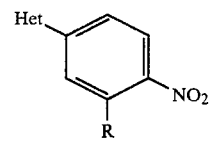

| Preparation No. | Het | R | Form isolated and m.p. (°C.) | Analysis % (Theoretical in Brackets) | | |
|---|---|---|---|---|---|---|
| | | | | C | H | N |
| 40 | [CF3-substituted pyrazole-N] | —CH₃ | Free base, 147° | 48.6 (48.7 | 3.0 3.0 | 15.5 15.5) |
| 41 | [pyrazole-N] | —CH₃ | Free base, 0.66 H₂O 87–88° | 55.9 (55.8 | 4.6 4.8 | 19.7 19.5) |
| 42 | [3,5-dimethyl-1,2,4-triazole-N] | —CH₃ | Free base, 108–110° | 56.6 (56.9 | 5.3 5.2 | 23.8 24.1) |
| 43 | [tetrazole-N] | —CH₃ | Free base, 107–110° | 46.5 (46.8 | 3.5 3.4 | 34.4 34.2) |
| 44 | [2,5-dimethylimidazole-N] | —CF₃ | Free base, 169–171° | 50.6 (50.5 | 3.6 3.5 | 15.0 14.7) |

A mixture of 5-fluoro-2-nitrotoluene (10.3 g), 2,4-dimethylimidazole (6.36 g) and sodium carbonate (7.5 g) was heated with stirring in dimethylformamide (40 cm³) at 130° for 40 hours. The cooled mixture was then concentrated in vacuo, the residue was acidified to pH1 with 4M hydrochloric acid, and the resulting solution was extracted with chloroform (2×25 cm³) to remove any neutral material. The combined aqueous phases were basified to pH10 with 2.5 M sodium hydroxide solution and the mixture was extracted with chloroform (3 x 250 cm³). The combined and dried (MgSO₄) organic extracts were concentrated in vacuo to give a solid which was chromatographed on silica (Merck "MK 60.9385" [Trade Mark]) eluting with methanol:ethyl acetate, 1:19. Combination and evaporation of appropriate fractions afforded a solid (8.4 g) which was recrystallised from ethyl acetate to give 1-(3-methyl-4-nitrophenyl)-2,4-dimethylimidazole, m.p. 135.5°–138°.

Analysis %: Found: C,62.0; H,5.7; N,17.9; Calculated for C₁₂H₁₃N₃0₂: C,62.3; H,5.7; N,18.2.

PREPARATION 45

4-(3-Methyl-4-nitrophenyl)-1,2,4-triazole

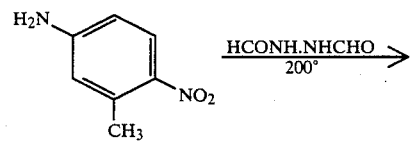

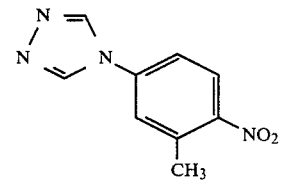

A mixture of 5-amino-2-nitrotoluene (2.0 g) and 1,2-diformylhydrazine (1.3 g) was heated under nitrogen for 1 hour at 200°. The residue was then cooled and chromatographed on silica (Merck "MK 60.9385" [Trade Mark]) eluting with methanol:dichloromethane, 1:19. Combination and evaporation of appropriate fractions gave a solid (1.03 g) which was recrystallised from ethanol to afford 4-(3-methyl-4-nitrophenyl)-1,2,4-triazole, m.p. 208°-b 210°.

Analysis %: Found: C,52.8; H,4.0; N,27.3; Calculated for $C_9H_8N_4O_2$: C,52.9; H,3.9; N,27.4.

PREPARATION 46

4-(4-Nitro-3-trifluoromethylphenyl)-1,2,4-triazole

The following compound m.p. 100°, was prepared similarly to the previous Preparation using 4-nitro-3-trifluoromethylaniline and 1,2-diformylhydrazine as the starting materials:

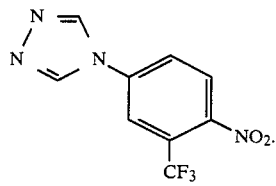

Analysis %: Found: C,41.9; H,2.0; N,21.7; Calculated for $C_9H_5N_4F_3O_2$: C,41.6; H,2.1; N,22.2.

PREPARATION 47

1-(3-Methyl-4-nitrophenyl)tetrazole

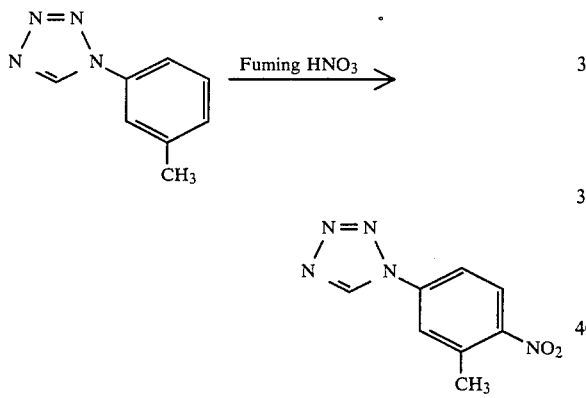

1-(3-Methylphenyl)tetrazole (11.3 g) was cautiously added at 0° to fuming nitric acid (100 cm³) with starting and the solution was then warmed on a steam bath for 5 minutes. The cooled solution was poured onto ice (200 g), and the solid material was filtered off, washed with water (100 cm³) and dried. Recrystallisation from ethyl acetate afforded 1-(3-methyl-4-nitrophenyl)tetrazole, m.p. 166°-168° (9.4 g).

Analysis %: Found: C,47.0; H,3.5; N,34.3; Calculated for $C_{18}H_7N_5O_2$: C,46.8; H,3.4; N,34.2.

1-(3-Methylphenyl)tetrazole is a known compound.

PREPARATION 48

6-Amino-2-methoxy-8-methylquinoline

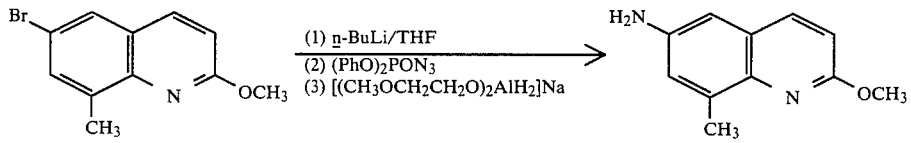

n-Butyllithium (13.75 cm³) of a 1.6 M solution in n-hexane) was added dropwise to a stirred solution of 6-bromo-2-methoxy-8-methylquinoline (5.04 g) in tetrahydrofuran (THF) (50 cm³) at −70° under nitrogen. After 15 minutes the fine suspension was transferred via a cannula to a stirred solution of diphenylphosphorylazide (5.5 g) in THF (50 cm³) at −70° under nitrogen. The dark solution was stirred at −70° for 2 hours, warmed to −20° over 1 hour and then re-coded at −70°. A solution of sodium bis(2-methoxyethoxy)aluminium hydride (23.5 cm³of a 3.4 M solution in toluene) was slowly added and the solution was warmed to room temperature over 1.5 hours. The mixture was cooled to 0°, ice (100 g) was cautiously added, the resulting suspension was filtered, and the solid was washed with ethyl acetate. The aqueous filtrate was further extracted with ethyl acetate (2×100 cm³) and the combined and dried (MgSO₄) organic extracts were evaporated in vacuo to give a residue which was chromatographed on silica (Merck "MK 60.9385" [Trade Mark]). Elution with toluene, followed by combination and evaporation of appropriate fractions, gave a solid which was recrystallised from hexane to afford 6-amino-2-methoxy-8-methylquinoline, m.p. 115°-117° (1.07 g).

Analysis %: Found: C,69.8; H,6.5; N,14.8; Calculated for $C_{11}H_{12}N_2O$: C,70.2; H,6.4; N,14.9.

PREPARATION 49

6-Acetamido-2-methoxy-8-methylquinoline

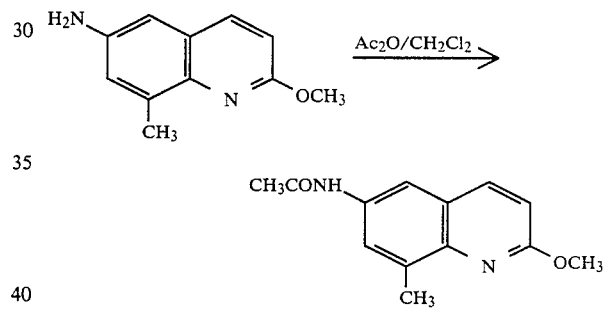

A solution of acetic anhydride (0.55 cm³) in dichloromethane (20 cm³) was added dropwise to a stirred solution of 6-amino-2-methoxy-8-methylquinoline (1.0 g) in dichloromethane (30 cm³) at room temperature. After 1 hour the solution was diluted with dichloromethane (50 cm³), washed with saturated sodium carbonate solution (10 cm³), and dried (MgSO₄). Evaporation of the solution in vacuo afforded to a solid which was recrystalised from dichloromethane/hexane to give 6-acetamido-2-methoxy-8-methylquinoline, m.p. 193°-196° (1.143 g).

Analysis %: Found: C,67.6; H,6.2; N,12.2; Calculated for $C_{13}H_{14}N_2O_2$: C,67.8; H,6.1; N,12.2.

PREPARATION 50

6-[3,5-Dimethyl-1,2,4-triazol-4-yl]-2-methoxy-8-methylquinoline, 1/6 H₂O

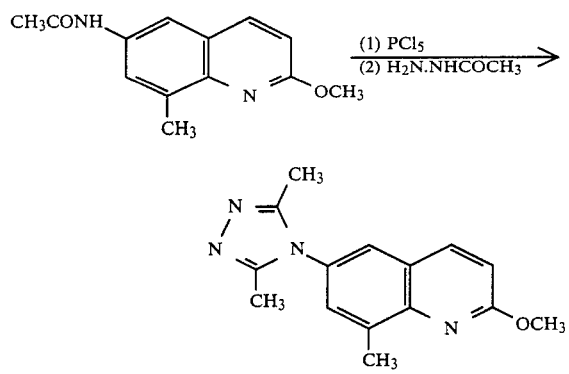

Phosphorous pentachloride (1.0 g) was added to a stirred solution of 6-acetamido-2-methoxy-8-methylquinoline (1.0 g) in toluene (50 cm³) and the mixture was stirred at 50° for 15 minutes. Acetyl hydrazine (1.35 g) was then added and the mixture was stirred for 3 hours at 60°. The toluene was removed in vacuo, the residue dissolved in ethanol, and aqueous ammonia solution (S.G. 0.88) (25 cm³) was added. Dichloromethane (100 cm³) was added and the organic phase was separated. The aqueous phase was further extracted with dichloromethane (2×25 cm³), and the combined organic phases were dried (MgSO₄) and evaporated to give a solid which was chromatographed on silica (Merck "MK 60.9385" [Trade Mark]) eluting with dichloromethane:methanol, 19:1. Combination and evaporation of appropriate fractions afforded 6-[3,5-dimethyl-1,2,4-triazol-4-yl]-2-methoxy-8-methylquinoline (0.306 g), which was recrystallised from toluene to give microcrystals, m.p. 211°–213° (0.066 g).

Analysis %: Found: C,66.6; H,5.9; N,20.6; Calculated for $C_{15}H_{16}N_4O.1/6\ H_2O$: C,66.4; H,6.0; N,20.7.

PREPARATION 51

2-Methoxy-8-methyl-6-[1,2,4-triazol-4-yl]-quinoline, 0.25 H₂O

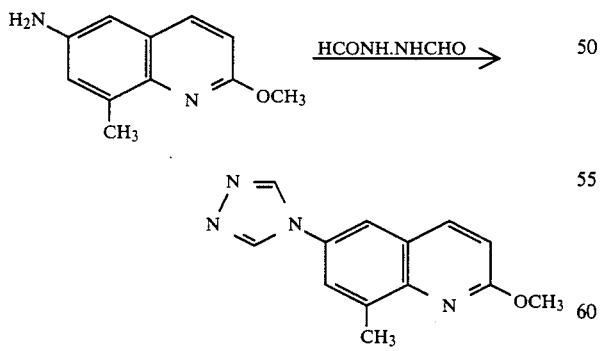

An intimate mixture of 1,2-diformylhydrazine (2.93 g) and 6-amino-2-methoxy-8-methylquinoline (5.4 g) was heated at 200° for 1 hour. The cooled residue was chromatographed on silica (Merck "MK 60.9385") eluting with dichloromethane:methanol, 50:1. Combination and evaporation of the fractions having an $R_F$ of 0.44 (dichloromethane:methanol, 19:1) gave, as a by-product, 6-formamido-2-methoxy-8-methylquinoline (1.35 g) which was recrystallised from toluene to afford white microcrystals, m.p. 142°–143.5° (0.67 g).

Analysis %: Found: C,66.5; H,5.6; N,13.0; Calculated for $C_{12}H_{12}N_2O_2$: C,66.6; H,5.6; N,13.0.

Further elution of the column gave a second fraction $R_F$ 0.3 (dichloromethane:methanol, 19:1) which was evaporated to give a solid (1.2 g). Recrystallisation of the solid from ethyl acetate afforded 2-methoxy-8-methyl-6-[1,2,4-triazol-4-yl]-quinoline, 0.25 H₂O, m.p. 157°–159° (0.73 g).

Anslysis %: Found: C,64.1; H,5.1; N,22.6; Calculated for $C_{13}H_{12}N_4O.0.25\ H_2O$: C,63.8; H,5.1; N,22.9.

PREPARATION 52

6-Bromo-2-methoxy-8-methylquinoline

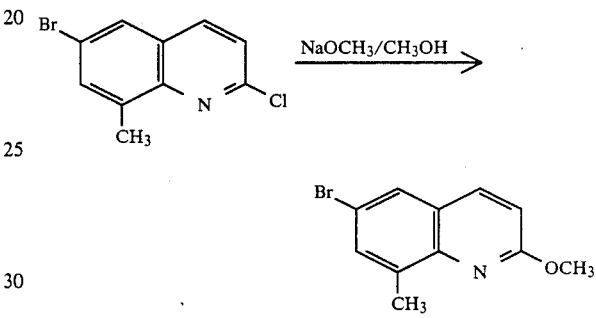

A solution of 6-bromo-2-chloro-8-methylquinoline (10.7 g) in methanol (80 cm³) was heated under reflux with a solution of sodium methoxide [made from sodium 2.76 g) in methanol (50 cm³)]for 24 hours. The cooled solution was then evaporated in vacuo and the residue was partitioned between chloroform (100 cm³) and water (50 cm³). The aqueous phase was further extracted with chloroform (2×50 cm³) and the combined and dried (MgSO₄) organic phases were evaporated in vacuo to give a solid which was recrystallised from ethyl acetate:hexane, 1:9, to afford 6-bromo-2-methoxy-8-methylquinoline, m.p. 89°–91° (8.3 g).

Analysis %: Found: C,52.2; H,3.9; N,5.7; Calculated for $C_{11}H_{10}BrNO$: C,52.4; H,4.0; N,5.6.

PREPARATION 53

6-Bromo-2-chloro-8-methylquinoline

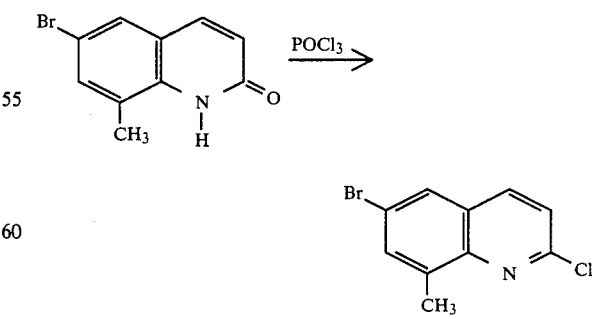

A mixture of 6-bromo-8-methyl-2-(1H)-quinolone (12.0 g) in phosphorus oxychloride (100 cm³) was heated under reflux for 2 hours. Volatile material was removed in vacuo, the residue dissolved in chloroform (200 cm³), and the resulting solution was poured into ice (200 g). The mixture was basified with aqueous ammonia solution (S.G. 0.88) to pH10 and the aqueous phase was further extracted with chloroform (2×100 cm³). The combined and dried (MgSO₄) organic phases were concentrated in vacuo to give a solid (10.7 g) which was recrystallised from ethanol to afford 6-bromo-2-chloro-8-methylquinoline, m.p. 114°–116°.

Analysis %: Found: C,47.2; H,2.7; N,5.8; Calculated for C₁₀H₇BrClN: C,46.8; H,2.7; N,5.5.

PREPARATION 54

6-Bromo-8-methyl-2-(1H)-quinolone

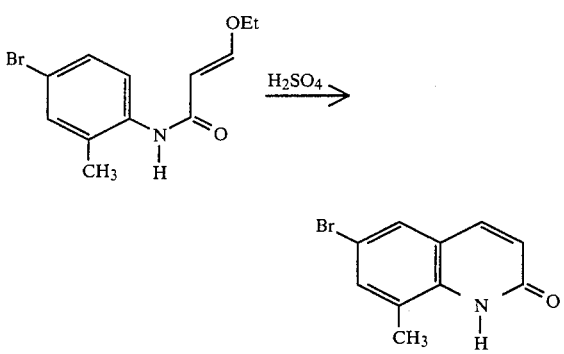

Trans-N-(4-bromo-2-methylphenyl)-3-ethoxypropenamide (2.0 g) was added portionwise with stirring to 98% sulphuric acid (15 cm³) at room temperature. After 16 hours the solution was poured onto ice (100 cm³) and the resulting precipitate was filtered off and dried (1.5 g). Recrystallisation from ethyl acetate-methanol afforded 6-bromo-8-methyl-2-(1H)-quinolone, m.p. 272°–274°.

Analysis %: Found: C,50.4; H,3.4; N,6.1; Calculated for C₁₀H₈NOBr: C,50.4; H,3.4; N,5.9.

PREPARATION 55

Trans-N-(4-Bromo-2-methylphenyl)-3-ethoxypropenamide

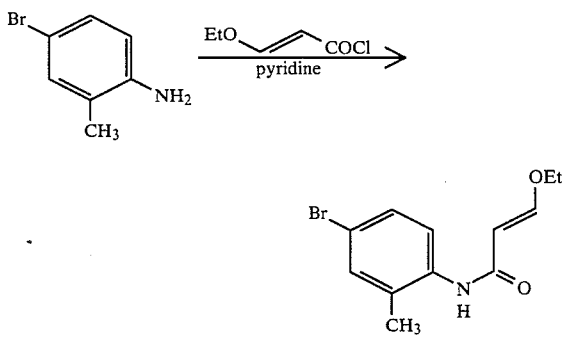

Trans-3-Ethoxypropenoyl chloride (0.74 g) was added at 0° to a stirred solution of 4-bromo-2-methylaniline (0.93 g) in pyridine (10 cm³). After 0.5 hours water (40 cm³) was added, the solid material was filtered off, washed with water (30 cm³) and dried. The product was recrystallised from ethyl acetate to afford trans-N-(4-bromo-2-methylphenyl)-3-ethoxypropenamide, m.p. 163°–164°, (1.3 g).

Analysis %: Found: C,50.7; H,5,0; N,5.0; Calculated for C₁₂H₁₄NO₂Br: C,50.7; H,5.0; N,4.9.

PREPARATION 56

1-(4-Amino-3-trifluoromethylphenyl)-2,4-dimethylimidazole

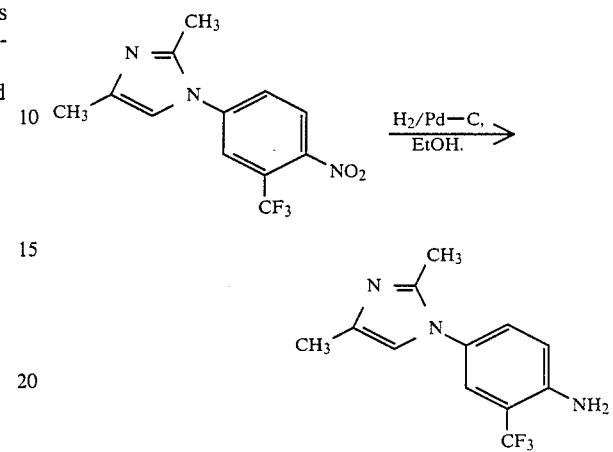

Ethanol (300 cm³) was added to 1-(4-nitro-3-trifluoromethyl-phenyl)-2,4-dimethylimidzole (29.0 g) and the mixture was hydrogenated at 50° and 50 p.s.i. (3.23×10⁵Pa) pressure over 5% paladised charcoal (2 g) for 16 hours. The mixture was then filtered through "Solkafloc" (Trade Mark), and the solvent evaporated in vacuo to give a pale yellow solid (25.8 g). A small sample was recrystallised from ethyl acetate/hexane to give 1-(4-amino-3-trifluoromethylphenyl)-2,4-dimethylimidazole, m.p. 126°–7°.

Analysis %: Found: C,56.5; H,4.8; N,16.6; Calculated for C₁₂H₁₂N₃F₃: C,56.5; H,4.7; N,16.5.

PREPARATION 57

4-(4-Amino-3-trifluoromethylphenyl)-1,2,4-triazole

The following compound, m.p. 196°–8°, was prepared similarly to the previous Preparation using 4-(4-nitro-3-trifluoromethylphenyl)-1,2,4-triazole and 5% palladised charcoal/H₂ as the starting materials:

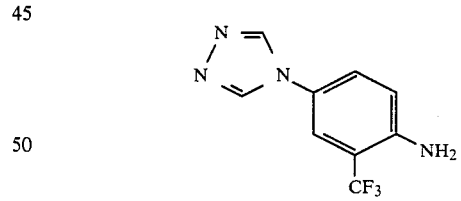

Analysis %: Found: C,47.7; H,3.2; N,24.9; Calculated for C₉H₇N₃F₃: C,47.4; H,3.1; N,24.6.

PREPARATION 58 (Alternative to Preparation 32)

1-(4-Amino-3-methylphenyl)-2,4-dimethylimidazole

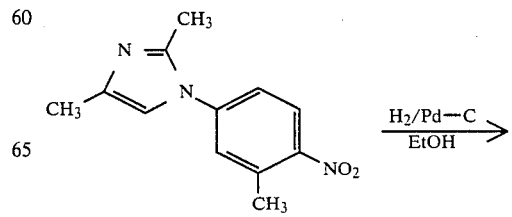

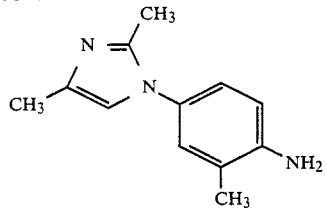

The following compound was prepared similarly to Preparation 56, using 1-(3-methyl-4-nitrohenyl)-2,4-dimethylimidazole and 5% palladised charcoal/$H_2$ as the starting materials and ethanol as the solvent. The crude solid melted at 78°–82°. Recrystallisation from toluene gave 1-(4-amino-3-methylphenyl)-2,4-dimethylimidazole, m.p. 118°–120° C.

Analysis %: Found: C,71.0; H,7.6; N,20.8; Calculated for $C_{11}H_{15}N_3$: C,71.6; H,7.5; N,20.9.

PREPARATION 59

Trans-ethyl 3-(2-amino-3-trifluoromethyl-5-[1,2,4-triazol-4-yl]phenyl)prop-2-enoate The following compound, m.p. 225°–7°, was prepared similarly to Example 37 using 4-(3-formyl-4-amino-5-trifluoromethylphenyl)-1,2,4-triazole, triethyl phosphonoacetate and sodium hydride as the starting materials.

[In this reaction, only a trace of 8-trifluoromethyl-6-(1,2,4-triazol-4-yl)-2-(1H)-quinolone was produced.]

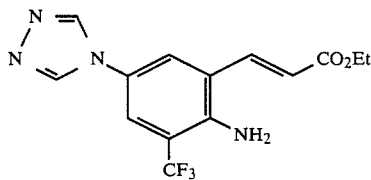

PREPARATION 60

1-(4-Amino-3-iodo-5-methylphenyl)tetrazole

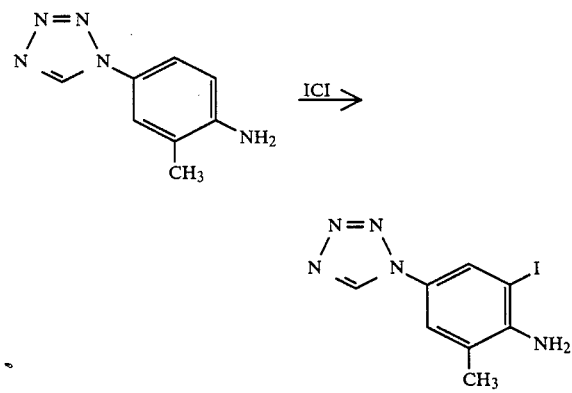

A solution of iodine monochloride (4.46 g) in acetic acid (30 cm³) was added dropwise to a stirred solution of 2-methyl-4-(tetrazol-1-yl)aniline (4 g) in acetic acid (30 cm³). After 2 hours the mixture was brought to pH 6 by addition of aqueous sodium carbonate solution and extracted with dichloromethane (250 cm³). The organic phase was dried (MgSO₄), filtered and evaporated to yield a dark brown solid. This solid was chromatographed on silica (Merck "MK 60.9385" [Trade Mark]) eluting with dichloromethane to afford 1-(4-amino-3-iodo-5-methylphenyl)tetrazole, m.p. 172°–175°, (6.2 g).

Analysis %: Found: C,32.1; H,2.7; N,23.4; Calculated for $C_8H_8N_5I$: C,31.9; H,2.7; N,23.3.

PREPARATION 61

2-(4-Amino-3-iodo-5-methylphenyl)tetrazole

The following compound, m.p. 196°–199° was prepared similarly to the previous Preparation using 2-(4-amino-3-methylphenyl)tetrazole and iodine monochloride as the starting materials:

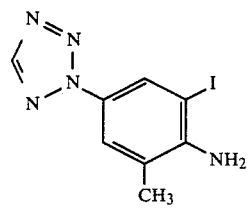

Analysis %: Found: C,31.9; H,2.7; N,23.3; Calculated for $C_8H_8N_5I$: C,31.9; H,2.7; N,23.3.

PREPARATION 62

Trans-ethyl 3-(2-amino-3-methyl-5-[tetrazol-1-yl]phenyl)prop2-enoate

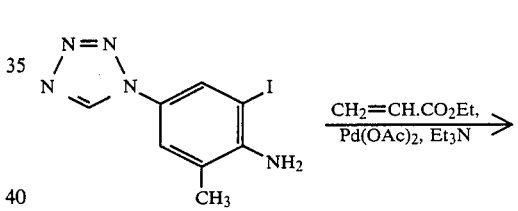

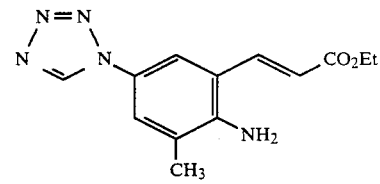

To solution of 1-(4-amino-3-iodo-5-methylphenyl)tetrazole (5 g) in acetonitrile (80 cm³) was added ethyl acrylate (2 g), triethylamine (2 g) and palladium acetate (0.1 g). The mixture was heated under reflux for 1½ hours, cooled and then partitioned between water (100 cm³) and dichloromethane (100 cm³). The aqueous phase was re-extracted with more dichloromethane (100 cm³) and the combined organic phase were dried (MgSO₄), filtered and evaporated in vacuo. The residue was chromatographed on silica (Merck "MK 60.9385" [Trade Mark]) eluting with dichloromethane: methanol, 20:1. Combination and evaporation of appropriate fractions gave a solid which on recrystallisation from ethyl acetate/methanol afforded yellow needles of trans-ethyl 3-(2-amino-3-methyl-5-[tetrazol-1-yl]phenyl)prop-2-enoate, m.p. 210°–211°, (3.45 g).

Analysis %: Found: C,56.0; H,5.6; N,25.7; Calculated for $C_{13}H_{15}N_5O_2$: C,57.1; H,5.5; N,25.6.

PREPARATION 63

Trans-ethyl 3-(2-amino-3-methyl-5-[tetrazol 2-yl]phenyl)prop2-enoate, 0.16 H$_2$O The following compound, m.p. 162°–5°, was prepared similarly to the previous Preparation using 2-(4-amino-3-iodo-5-methylphenyl)tetrazole, ethyl, acrylate, palladium acetate and triethylamine as the starting materials:

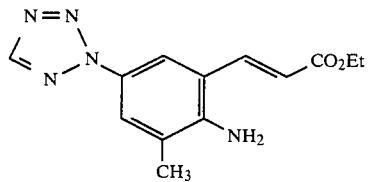

Analysis %: Found: C,56.5; H,5.5; N,25.7; Calculated for C$_{13}$H$_{15}$N$_5$O$_2$.0.16 H$_2$O: C,56.5; H,5.7; N,25.4.

PREPARATION 64

4-Nitro-3-trifluoromethylaniline

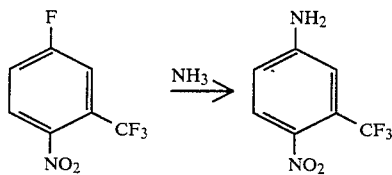

A solution of ammonia in water (100 cm$^3$, s.g. 0.88) was added to 3-trifluoromethyl-4-nitrofluorobenzene (5 g) and the mixture was heated in a bomb at 150° for 2 hours. Solvent was removed in vacuo to yield a yellow solid. Recrystallisation of this solid from hexane/ethyl acetate afforded yellow crystals of 4-nitro-3-trifluoromethylaniline, m.p. 134°, (3.5 g).

Analysis %: Found: C,41.0; H,2.4; N,13.5; Calculated for C$_7$H$_5$N$_2$F$_3$: C,40.8; H,2.4; N,13.6.

3-Trifluoromethyl-4-nitrofluorobenzene is a known compound.

PREPARATION 65

1-(3-Bromo-4-amino-5-trifluoromethylphenyl)-2,4-dimethylimidazole

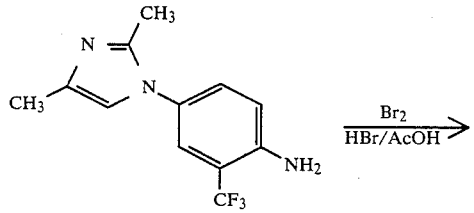

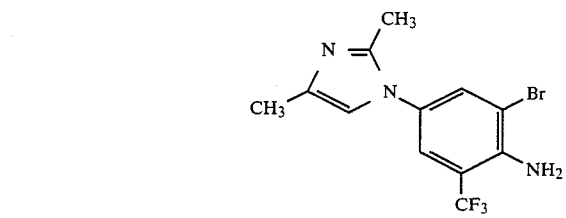

1-(4-Amino-3-trifluoromethylphenyl)-2,4-dimethylimidazole (10 g) was dissolved in glacial acetic acid (70 cm$^3$). A solution of 45% w/w hyrdogen bromide in glacial acetic acid (7.4 cm$^3$) was added. A solution of bromine (2.1 cm$^3$)in glacial acetic acid (30 cm$^3$) was then added dropwise. The mixture was heated at 70° for 3 hours, cooled, concentrated to a small volume by evaporation in vacuo, and basified to pH 8 by addition of aqueous sodium carbonate solution. The aqueous phase was extracted with chloroform (3×200 cm$^3$) and the combined organic extracts were dried (MgSO$_4$) and evaporated in vacuo. The residue was chromatographed on silica (Merck "MK 60.9385" [Trade Mark]), eluting with ethyl acetate. Combination and evaporation of appropriate fractions afforded 1-(3-bromo-4-amino-5-trifluoromethylphenyl)-2,4-dimethylimidazole (4.76 g), a small sample of which was recrystallised from ethyl acetate/hexane, m.p. 149°.

Analysis %: Found: C,43.0; H,3.5; N,12.5; Calculated for C$_{12}$H$_{11}$N$_3$F$_3$Br: C,43.1; H,3.3; N,12.6.

PREPARATION 66

4-(4-Amino-3-bromo-5-trifluoromethylphenyl)-1,2,4-triazole

The following compound, m.p. 202°–3°, was prepared similarly to the previous Preparation using 4-(4-amino-3-trifluoromethylphenyl)-1,2,4-triazole, bromine, and sodium acetate (in place of hydrogen bromide and acetic acid) as the starting materials:

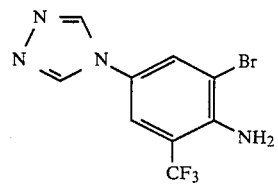

Analysis %: Found: C,35.4; H,2.0; N,18.3; Calculated for C$_9$H$_6$N$_4$F$_3$Br: C,35.2; H,2.0; N,18.3.

PREPARATION 67

1-(4-Amino-3-cyano-5-trifluoromethylphenyl)-2,4-dimethylimidazole

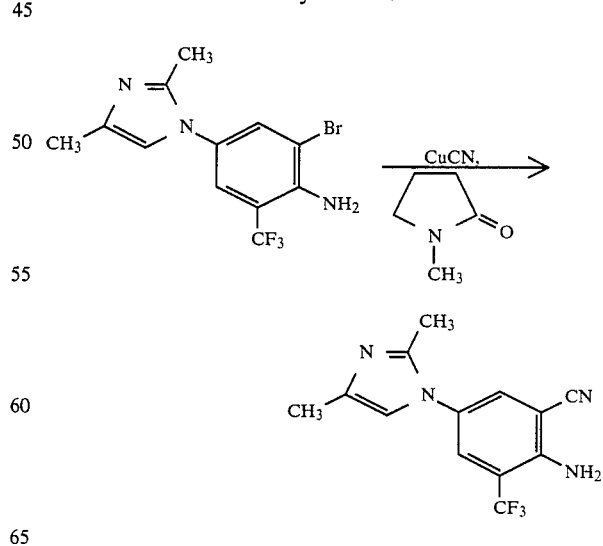

To a stirred solution of 1-(4-amino-3-bromo-5-trifluoromethylphenyl)-2,4-dimethylimidazole (4.61 g) in 1-methyl-2-pyrrolidone (50 cm$^3$) was added cuprous cyanide (3.7 g) and the mixture was heated at 150° for 2 days. The mixture was then cooled and the solvent evaporated in vacuo. A solution of ammonia in water (100 cm³, s.g. 0.88) was added and the aqueous phase was extracted with chloroform:methanol, 20:1 (3×100 cm³). The combined organic extracts were dried (MgSO₄), filtered and evaporated. The residue was chromatographed on silica (Merck "MK 60.9385" [Trade Mark]) eluting with chloroform: methanol, 50:1. Combination and evaporation of appropriate fractions gave a solid which was recrystallised from methanol-/ethyl acetate to give microcrystals of 1-(4-amino-3-cyano-5-trifluoromethylphenyl)2,4-dimethylimidazole, (1.1 g), m.p. 208°–10°.

Analysis %: Found: C,55.7; H,4.0; N,19.7; Calculated for $C_{13}H_{11}N_4F_3$: C,55.7; H,4.0; N,20.0.

PREPARATION 68

4-(4-Amino-3-cyano-5-trifluoromethylphenyl)-1,2,4-triazole

The following compound, m.p. 283°, was similarly prepared to the prevous Preparation using 4-(4-amino-3-bromo-5-trifluoromethylphenyl)-1,2,4-triazole, cuprous cyanide and 1-methyl-2-pyrrolidone as the starting materials:

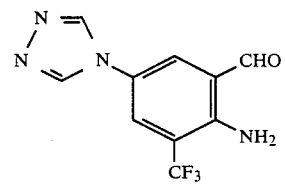

Analysis %: Found: C,47.3; H,2.5; N,27.3; Calculated for $C_{10}H_6N_5F_3$: C,47.4; H,2.4; N,27.7.

PREPARATION 69

1-(4-Amino-3-formyl-5-trifluoromethylphenyl)-2,4-dimethylimidazole

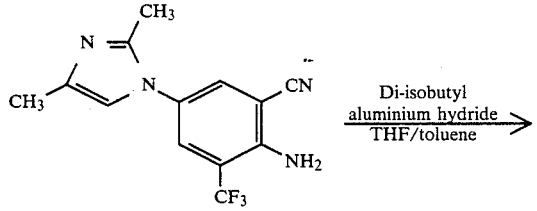

To an ice-cooled stirred solution of 1-(4-amino-3-cyano-5-trifluoromethylphenyl)-2,4-dimethylimidazole (0.7 g) in tetrahydrofuran (10 cm³) was added 3.5 cm³of a 1.5 M solution of diisobutyl aluminium hydride in toluene. The mixture was heated at 40° for 2 hours, cooled in ice, treated with methanol (2 cm³), and evaporated in vacuo. The residue was treated with water (25 cm³) and 2M hydrochloric acid (5 cm³), and heated on a steam bath for five minutes. The solution was then cooled, basified to pH 8 with aqueous sodium carbonate solution, and extracted with chloroform:methanol, 20:1 (3×30 cm³). The combined organic extracts were dried (MgSO₄), evaporated in vacuo, and the residue was chromatographed on silica (Merck "MK 60.9385" [Trade Mark]) eluting with ethyl acetate:methanol, 50:1, to afford 1-(4-amino-3-formyl-5-trifluoromethylphenyl)-2,4-dimet m.p. 200°–202°, (0.391 g).

Analysis %: Found: C,54.6; H,4.3; N,14.4; Calculated for $C_{13}H_{12}F_3N_3O$: C,55.1; H,4.3; N,14.8.

PREPARATION 70

4-(4-Amino-3-formyl-5-trifluoromethylphenyl)-1,2,4-triazole

The following compound, m.p. 234°–6°, was prepared similarly to the previous Preparation using 4-(4-amino-3-cyano-5-trifluoromethylphenyl)-1,2,4-triazole and diisobutyl aluminium hydride as the starting materials:

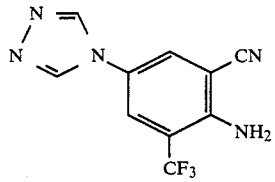

Further Examples illustrating the invention are as follows:

EXAMPLES 43 AND 44

The following compounds were prepared similarly to Example 42 using 6-(2-methyl-4-iodolmidazol-1-yl)-or 6-(4-methyl-2-iodoimidazol-1-yl)-8-methyl-2-(1H)-quinolone, cuprous cyanide and palladium acetate as the starting materials with N-methyl-2-pyrrolidone as the solvent:

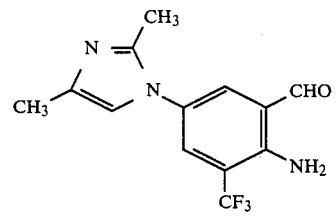

| Example No. | Het | Form Isolated and m.p. (°C.) | Analysis % (Theoretical in brackets) | | |
|---|---|---|---|---|---|
| | | | C | H | N |
| 43 | (CH₃, CN imidazole) | Free base 0.67H₂O, >350° | 65.3 (65.2 | 4.5 4.8 | 20.1 20.3) |
| 44 | (CN, CH₃ imidazole) | Free base, 0.17H₂O, 302-4°. | 67.5 (67.4 | 4.7 4.6 | 20.9 21.0) |

EXAMPLE 45

Preparation of 6-(2-iodo-4-methylimidazol-1-yl)-8-methyl-2-(1H)quinolone

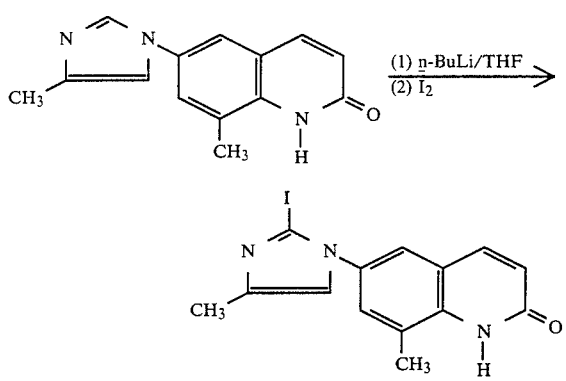

n-Butyllithium (2.94 cm³ of a 1.43 M solution in n-hexane was added dropwise to a stirred suspension of 6-(4-methylimidazol1-yl)-8-methyl-2-(1H)-quinolone (0.45 g) (see Example 6) in tetrahydrofuran (THF) (25 cm³) at −70° C. under nitrogen. After one hour iodine (0.51 g) was added and the mixture warmed to room temperature over 1.5 hours. Ammonium chloride solution was added (5 cm³), and the mixture was poured into water (20 cm³). The aqueous mixture was extracted with dichloromethane (3×50 cm³) and the combined and dried (MgSO₄) organic extracts were evaporated in vacuo to give a residue which was chromatographed on silica (Merck "MK 60.9385" [Trade Mark]). Elution with chloroform followed by combination and evaporation of appropriate fractions gave a solid which was recrystallised from ethyl acetate to afford 6-(2-iodo-4-methylimidazol-1-yl)-8-methyl-2-(1H)-quinolone, m.p. (d) 260° (0.22 g).

Analysis %: Found: C,44.7; H,3.6; N,10.8; Calculated for $C_{14}H_{12}N_3OI.2/3\ H_2O$: C,44.6; H,3.5; N,11.1.

EXAMPLE 46

6-(4-Iodo-2-methylimidazol-1-yl)-8-methyl-2-(1H)-quinolone, ⅓ H₂O, m.p. 285°–287°, was prepared similary to Example 12 starting from trans-1-[4-{N-(3-ethoxypropenamido)}-3-methylphenyl]-4-iodo-2-methylimidazole and 98% w/w sulphuric acid.

Analysis %: Found: C,45.3; H,3.3; N,11.3; Calculated for $C_{14}H_{12}N_3OI.1/3\ H_2O$: C,45.3; H,3.4; N,11.3.

The following illustrates the preparation of certain starting materials for Examples 43 to 46:

PREPARATION 71

Trans-1-[4-{N-(3-ethoxypropenamido)}-3-methylphenyl]-4-iodo-2-methylimidazole, m.p. 172°–174°, was prepared similarly to Preparation 1 using 1-(4-Amino-3-methylphenyl)-4-iodo-2-methylimidazole and trans-3-ethoxypropenoyl chloride as the starting materials with anhydrous pyridine as the solvent.

Analysis %: Found: C,46.8; H,4.5; N,10.1; Calculated for $C_{16}H_{18}N_3O_2I$: C, 46.7; H,4.4; N,10.2.

PREPARATION 72

1-(4-Amino-3-methylphenyl)-4-iodo-2-methylimidazole, isolated and later used as a crude oil, was prepared similarly to Preparation 12 using 1-(3-Methyl-4-nitrophenyl)-4-iodo-2-methylimidazole and stannous chloride dihydrate as the starting materials with absolute ethanol as the solvent.

PREPARATION 73

1-(3-Methyl-4-nitrophenyl)-4-iodo-2-methylimidazole, m.p. 146°–148°, was prepared similarly to Preparation 20 using using 4-fluoro-2-methylnitrobenzene, 4-iodo-2-methylimidazole and sodium carbonate as the starting materials with dimethylformamide as the solvent.

Analysis %: Found: C,38.5; H,3.1; N,12.4; Calculated for $C_{11}H_{10}N_3O_2I$: C,38.5; H,2.9; N,12.2;

PREPARATION 74

4-Iodo-2-methylimidazole

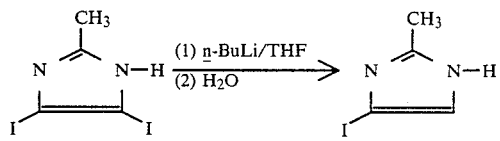

n-Butyllithium (86 cm³ of a 1.43 M solution is n-hexane) was added dropwise to a stirred solution of 4,5-diiodo-2-methylimidazole (20.5 g) in tetrahydrofuran (THF) (300 cm³) at −70° under nitrogen. After 15 minutes water (20 cm³) was added and the mixture was warmed to room temperature over 1 hour. The mixture was then evaporated in vacuo to low bulk, more water (50 cm³) was added, and the pH was adjusted to 8 by addition of 2M hydrochloric acid. The aqueous phase was extracted with dichloromethane (3×150 cm³), and the combined and dried (MgSO₄) organic extracts were evaporated in vacuo to give a residue which was chromatographed on silica (Merck "MK 60.9385" [Trade Mark]). Elution with ethyl acetate followed by combination and evaporation of appropriate fractions, gave 4-iodo-2-methylimidazole as a solid (9.0 g) which was characterised spectroscopically and used directly without further purification.

PREPARATION 75

4,5-Diiodo-2-methylimidazole

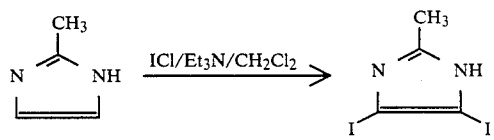

A solution of iodine monochloride (32.5 g) dissolved in dichloromethane (100 cm³)was added dropwise over 1.5 hours to a solution of 2-methylimidazole (8.2 g) and triethylamine (20.2 g) in dichloromethane (200 cm³) at −70° under nitrogen. The mixture was stirred for a further 30 minutes, warmed to −30°, and then poured into water (200 cm³). The resulting precipitate was filtered off, dried and recrystallised from ethyl acetate-hexane to afford 4,5-diiodo-2-methylimidazole (18.5 g) which was characterised spectroscopically and used directly without further purification.

We claim:

1. An N-(ring-substituted phenyl)propenamide compound of the formula:

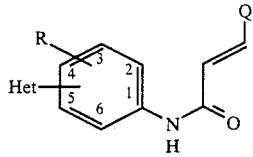

or an acid addition salt thereof, wherein (a) "Het" is an imidazolyl or triazolyl group attached by a nitrogen atoms of said group to the 3-, 4-, 5- or 6-positions of said phenyl ring, said heterocyclic groups being unsubstituted or substituted with up to three substituents each independently selected from $C_1$–$C_4$ alkyl, $C_1$–$C_4$ alkoxy, hydroxy, trifluoromethyl, halo, cyano, hydroxymethyl, ($C_1$–$C_4$ alkoxy)carbonyl, nitro, -CONR$^1$R$^2$ and -NR$^1$R$^2$ wherein R$^1$ and R$^2$ are each independently hydrogen or $C_1$–$C_4$ alkyl; and (b) R is hydrogen, $C_1$–$C_4$ alkyl, $C_1$–$C_4$ alkoxy, hydroxy, trifluoromethyl, halo, cyano or hydroxymethyl, said R being attached to the 3-, 4-, 5-, or 6-positions of the aforesaid phenyl ring; and (c) Q is a $C_1$–$C_4$ alkoxy group.

2. A compound as claimed in claim 1 wherein (a) "Het" is imidazol-1-yl, 2-methylimidazol-1-yl, 4-methylimidazol-1-yl or 1,2,4-triazol-1-yl; (b) R is hydrogen, and (c) Q is ethoxy.

3. A compound as claimed in claim 1 wherein (a) "Het" is imidazol-1-yl, 2-methylimidazol-1-yl, 4-methylimidazol-1-yl, 5-methylimidazol-1-yl, 2,4-dimethylimidazol-1-yl, 4-trifluoromethylimidazol-1-yl, 4-iodo-2-methylimidazol-1-yl, 1,2,4-triazol-1-yl, 1,2,4-triazol-4-yl or 3,5-dimethyl-1,2,4-triazol-1-yl; (b) R is methyl, and (c) Q is ethoxy.

4. A compound as claimed in claim 3 wherein "Het" is 2,4-dimethylimidazol-1-yl.

5. A compound as claimed in claim 3 wherein "Het" is 1,2,4-triazol-4-yl.

6. Trans-1-[4-{N-(2-ethoxypropenamido)}-3-methylphenyl]2,4-dimethylimidazole.

* * * * *